US011039732B2

(12) United States Patent
Imai

(10) Patent No.: US 11,039,732 B2
(45) Date of Patent: Jun. 22, 2021

(54) ENDOSCOPIC SYSTEM AND METHOD OF OPERATING SAME

(71) Applicant: FUJIFILM Corporation, Tokyo (JP)

(72) Inventor: Yoshiro Imai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 348 days.

(21) Appl. No.: 16/109,797

(22) Filed: Aug. 23, 2018

(65) Prior Publication Data

US 2019/0008361 A1 Jan. 10, 2019

Related U.S. Application Data

(63) Continuation of application No. PCT/JP2017/002677, filed on Jan. 26, 2017.

(30) Foreign Application Priority Data

Mar. 18, 2016 (JP) .............................. JP2016-054631

(51) Int. Cl.
*A61B 1/00* (2006.01)
*H04N 7/18* (2006.01)
(Continued)

(52) U.S. Cl.
CPC ........ *A61B 1/00009* (2013.01); *A61B 1/0005* (2013.01); *A61B 1/00006* (2013.01); *A61B 1/00055* (2013.01); *A61B 1/04* (2013.01); *A61B 1/045* (2013.01); *A61B 1/05* (2013.01); *A61B 1/0638* (2013.01); *A61B 1/0669* (2013.01);
(Continued)

(58) Field of Classification Search
CPC .......... H04N 5/23254; H04N 5/23264; H04N 5/23277; H04N 9/04521; A61B 1/00006; A61B 1/0005; A61B 1/00055
See application file for complete search history.

(56) References Cited

U.S. PATENT DOCUMENTS 4,699,125 A * 10/1987 Komatsu ............ H04N 5/23267
600/109
4,901,143 A * 2/1990 Uehara .............. H04N 9/04555
348/65
(Continued)

FOREIGN PATENT DOCUMENTS

JP 2011167349 9/2011
JP 2011194151 10/2011
(Continued)

OTHER PUBLICATIONS

"Search Report of Europe Counterpart Application", dated Feb. 21, 2019, p. 1-p. 8.
(Continued)

*Primary Examiner* — Timothy J Neal
*Assistant Examiner* — Jae Woo
(74) *Attorney, Agent, or Firm* — JCIPRNET

(57) ABSTRACT

An image selection unit selects a B2 image signal of which an image blurring amount satisfies a first condition, from a B2 image signal at a first timing T1 or B2 image signals at the second timing T2 to an N-th timing TN. A computed image signal generation unit performs computation based on a B1 image signal at the first timing T1 and a second image signal selected in the image selection unit, thereby generating a computed image signal.

20 Claims, 14 Drawing Sheets

(51) Int. Cl.

| | |
|---|---|
| *G06T 5/00* | (2006.01) |
| *A61B 1/045* | (2006.01) |
| *A61B 1/05* | (2006.01) |
| *H04N 9/04* | (2006.01) |
| *G06T 5/50* | (2006.01) |
| *H04N 5/232* | (2006.01) |
| *A61B 1/04* | (2006.01) |
| *A61B 1/06* | (2006.01) |
| *A61B 1/07* | (2006.01) |
| *H04N 5/225* | (2006.01) |

(52) U.S. Cl.
CPC ............ *A61B 1/0684* (2013.01); *A61B 1/07* (2013.01); *G06T 5/003* (2013.01); *G06T 5/50* (2013.01); *H04N 5/23254* (2013.01); *H04N 5/23267* (2013.01); *H04N 7/18* (2013.01); *H04N 9/04521* (2018.08); *A61B 1/00186* (2013.01); *A61B 1/00188* (2013.01); *A61B 1/041* (2013.01); *G06T 2207/10024* (2013.01); *G06T 2207/10068* (2013.01); *G06T 2207/10152* (2013.01); *G06T 2207/30101* (2013.01); *H04N 2005/2255* (2013.01)

(56) References Cited

U.S. PATENT DOCUMENTS

| | | | | |
|---|---|---|---|---|
| 4,933,757 A * | 6/1990 | Kanno | ............... | H04N 5/23248 348/701 |
| 5,032,913 A * | 7/1991 | Hattori | ............... | H04N 5/23254 348/70 |
| 5,243,666 A * | 9/1993 | Hasegawa | ................ | A61B 1/05 348/65 |
| 10,039,439 B2 * | 8/2018 | Aoyama | ................ | H04N 9/045 |
| 10,646,110 B2 * | 5/2020 | Fukuda | .................... | A61B 1/05 |
| 10,779,734 B2 * | 9/2020 | Fengler | ............ | A61B 1/0638 |
| 10,805,553 B2 * | 10/2020 | Kudo | ..................... | H04N 5/243 |
| 10,891,743 B2 * | 1/2021 | Hirota | ..................... | G06T 5/007 |
| 2006/0268138 A1 * | 11/2006 | Higashitsutsumi | .. | H04N 5/3725 348/294 |
| 2007/0171279 A1 * | 7/2007 | Hasegawa | .............. | A61B 5/073 348/65 |
| 2008/0025640 A1 * | 1/2008 | Trudeau | ............. | H04N 5/23248 382/294 |
| 2008/0056613 A1 * | 3/2008 | Hatanaka | ........... | H04N 5/23254 382/284 |
| 2008/0095400 A1 * | 4/2008 | Nagano | ............ | H04N 5/23258 382/103 |
| 2008/0107358 A1 * | 5/2008 | Saito | .................. | H04N 5/23248 382/300 |
| 2008/0112644 A1 * | 5/2008 | Yokohata | ........... | H04N 5/23248 382/278 |
| 2008/0136939 A1 * | 6/2008 | Tamamura | ......... | H04N 5/23293 348/231.99 |
| 2008/0143840 A1 * | 6/2008 | Corkum | ............. | H04N 5/23248 348/208.6 |
| 2008/0158386 A1 * | 7/2008 | Miki | ..................... | H04N 5/2354 348/231.3 |
| 2008/0170124 A1 * | 7/2008 | Hatanaka | ........... | H04N 5/23248 348/208.4 |
| 2008/0187234 A1 * | 8/2008 | Watanabe | ............... | G06T 5/003 382/254 |
| 2011/0063460 A1 * | 3/2011 | Tokui | ................. | H04N 5/23277 348/208.4 |
| 2011/0237884 A1 | 9/2011 | Saito | | |
| 2011/0317043 A1 * | 12/2011 | On | ....................... | H04N 5/2256 348/241 |
| 2012/0189195 A1 * | 7/2012 | Paik | ......................... | G06T 5/50 382/164 |
| 2013/0058573 A1 | 3/2013 | Suzuki | | |
| 2013/0201315 A1 * | 8/2013 | Takei | ..................... | A61B 1/043 348/77 |
| 2014/0028861 A1 * | 1/2014 | Holz | ...................... | H04N 5/357 348/208.4 |
| 2014/0232912 A1 * | 8/2014 | Morimoto | ................. | G06T 5/20 348/270 |
| 2015/0054970 A1 * | 2/2015 | Hamada | .................. | G06T 5/002 348/208.1 |
| 2015/0216460 A1 | 8/2015 | Shigeta | | |
| 2016/0210731 A1 * | 7/2016 | Hamada | ............. | H04N 5/23254 |
| 2020/0170484 A1 * | 6/2020 | Kamon | ................ | A61B 1/0005 |

FOREIGN PATENT DOCUMENTS

| | | |
|---|---|---|
| JP | 2012239757 | 12/2012 |
| JP | 2015047402 | 3/2015 |
| JP | 2015146924 | 8/2015 |

OTHER PUBLICATIONS

"Office Action of Europe Counterpart Application," dated Oct. 9, 2019, p. 1-p. 5.

"International Search Report (Form PCT/ISA/210) of PCT/JP2017/002677", dated Feb. 28, 2018, with English translation thereof, pp. 1-4.

"Written Opinion of the International Searching Authority of PCT/JP2017/002677", with English translation thereof, dated Feb. 28, 2018, p. 1-p. 7.

* cited by examiner

ENDOSCOPIC SYSTEM AND METHOD OF OPERATING SAME

CROSS-REFERENCE TO RELATED APPLICATIONS

This application is a Continuation of PCT International Application No. PCT/JP2017/2677, filed on Jan. 26, 2017, which claims priority under 35 U.S.C. § 119(a) to Japanese Patent Application No. 2016-054631, filed on Mar. 18, 2016. Each of the above application(s) is hereby expressly incorporated by reference, in its entirety, into the present application.

BACKGROUND OF THE INVENTION

1. Field of the Invention

The present invention relates to an endoscope system and a method of operating the same.

2. Description of the Related Art

In the medical field, diagnosis using an endoscope system including a light source device, an endoscope, and a processor device has been performed widely. In the medical diagnosis using the endoscope system, an insertion part of the endoscope is inserted into a subject and an observation object is irradiated with illumination light from a distal end part of the endoscope. Then, the observation object under the irradiation with the illumination light is imaged by an imaging sensor of the distal end part, and an image of the observation object is generated using obtained image signals and displayed on a monitor.

Additionally, in recent years, new diagnosis using traveling patterns of blood vessels, or biological information, are being performed. For example, blood vessels at different depths, such as surface layer blood vessels, middle-depth blood vessels, and the like, which are important blood vessel patterns for diagnosis among traveling patterns of the blood vessels, are disclosed in JP5393525B (JP2011-167349A). In JP5393525B (JP2011-167349A), imaging is performed by irradiating the observation object with blue narrow-band light for extracting the surface layer blood vessels and green narrow-band light for extracting the middle-depth blood vessels at different timings. Also, in JP5393525B (JP2011-167349A), computation in which an image based on the blue narrow-band light and an image based on the green narrow-band light are weighted and added is performed so as to enhance blood vessels at a depth of interest.

Additionally, oxygen saturation having a high correlation with a lesion, such as cancer, even in the biological information is disclosed in JP5393554B (JP2011-194151A). In this JP5393554B (JP2011-194151A), imaging is performed by irradiating the observation object with light of different wavelength ranges including light of a wavelength range for measuring the oxygen saturation at different timings. Also, the oxygen saturation is calculated by performing computation using images based on the light of the different wavelength ranges.

SUMMARY OF THE INVENTION

In a case where observation is performed using the endoscope, a blurred image may be generated in an image in a moving image of the endoscope due to various kinds of blurring, such as blurring resulting from moving the endoscope and blurring resulting from a body motion of a subject. Such a blurred image becomes one of the factors that the decrease image quality of the moving image of the endoscope. Moreover, as shown in above Patent JP5393525B (JP2011-167349A) and JP5393554B (JP2011-194151A), in a case where various kinds of computation, such as weighted addition computation and oxygen saturation calculation computation, are performed on the basis of the image signals at the plurality of timings obtained by radiating the light of the different wavelength ranges at the different timings, there is a problem that the computation cannot be accurately performed in a case where a blurred image having a large amount of blurring is included even in one of the image signals at the plurality of timings.

As described above, regarding improvements in computation accuracy in a case where a blurred image is generated, there is no description or suggestion in related-art documents including JP5393525B (JP2011-167349A) and JP5393554B (JP2011-194151A). In addition, although JP5393554B (JP2011-194151A) describes that a positional deviation resulting from performing irradiation and imaging at the different timings is corrected there is no description regarding the computation accuracy in a case where blurring occurs, or no description regarding a method of improving the computation accuracy in a case where blurring occurs.

An object of the invention is to provide an endoscope system and a method of operating the same that can accurately perform computation even in a situation where a blurred image is generated, in a case where various kinds of computation are performed on the basis of image signals at a plurality of timings obtained by radiating light having different wavelength ranges at different timings.

An endoscope system of the invention comprises a light source that sequentially generates first illumination light and second illumination light; an imaging sensor that sequentially images an observation object illuminated sequentially with the first illumination light and the second illumination light at a first timing T1, thereby outputting multi-frame image signals at the first timing T1 and sequentially images the observation object illuminated sequentially with the first illumination light and the second illumination light at a specific timing before the first timing T1, thereby outputting multi-frame image signals at the specific timing; an image selection unit that selects a second image signal of which an image blurring amount satisfies a first condition from second image signals obtained in a case where the second illumination light is radiated among the multi-frame image signals at the first timing T1 and the specific timing; and a computed image signal generation unit that performs computation based on a first image signal obtained in a case where the first illumination light is radiated among the multi-frame image signals at the first timing T1 and the second image signal selected in the image selection unit, thereby generating a computed image signal.

It is preferable that the image selection unit selects a second image signal, of which the image blurring amount is less than a predetermined threshold value and which is imaged at a timing closest to the first timing T1, as the second image signal that satisfies the first condition. It is preferable that the image selection unit selects a second image signal with the smallest image blurring amount, as the second image signal that satisfies the first condition.

It is preferable that the image selection unit does not select the second image signal in a case where the second image signal of which the image blurring amount satisfies the first condition is not included in the multi-frame image signals at the first timing T1 and the specific timing, and the computed image signal generation unit generates the computed image signal only on the basis of the first image signal. It is preferable that the image selection unit does not select the second image signal in a case where the second image signal of which the image blurring amount satisfies the first condition is not included in the multi-frame image signals at the first timing T1 and the specific timing, and the computed image signal generation unit does not generate the computed image signal.

It is preferable that the endoscope system further comprises a warning display control unit that performs a control of displaying a warning in a case where the second image signal of which the image blurring amount satisfies the first condition is not included in the multi-frame image signals at the first timing T1 and the specific timing. It is preferable that the endoscope system further comprises an information display control unit that performs a control of displaying an image based on the second image signals included in the multi-frame image signals at the first timing T1 and the specific timing, and image blurring amounts of the second image signals at the first timing T1 and the specific timing on a display unit, in which the image selection unit has an auto-selection mode where the second image signal that satisfies the first condition is automatically selected, and a manual selection mode where a second image signal selected and indicated by a user is selected among the second image signals displayed on the display unit, and performs image selection in either the auto-selection mode or the manual selection mode.

An endoscope system of the invention comprises a light source that sequentially generates first illumination light and second illumination light; an imaging sensor that sequentially images an observation object illuminated sequentially with the first illumination light and the second illumination light at a first timing T1, thereby outputting multi-frame image signals at the first timing T1 and sequentially images the observation object illuminated sequentially with the first illumination light and the second illumination light at a specific timing before the first timing T1, thereby outputting multi-frame image signals at the specific timing; a blurring index value calculation unit that calculates blurring index values at the first timing T1 and the specific timing on the basis of an image blurring amount of a first image signal obtained in a case where the first illumination light is radiated and an image blurring amount of a second image signal obtained in a case where the second illumination light is radiated, among the multi-frame image signals at the first timing T1 and the specific timing; an image selection unit that selects a second image signal at a timing at which the blurring index values satisfy a second condition among the second image signals included in the multi-frame image signals at the first timing T1 and the specific timing; and a computed image signal generation unit that performs computation based on a first image signal included in the multi-frame image signals at the first timing T1 and a second image signal selected in the image selection unit, thereby generating a computed image signal.

It is preferable that in a case where the blurring index values are a blurring difference showing a difference between an image blurring amount of the first image signal and an image blurring amount of the second image signal, the image selection unit selects a second image signal at a timing at which the blurring difference is within a first specific range as the second image signal at the timing at which the second condition is satisfied, and in a case where the blurring index values are a blurring ratio showing a ratio of the image blurring amount of the first image signal and the image blurring amount of the second image signal, the image selection unit selects a second image signal at a timing at which the blurring ratio is within a second specific range as the second image signal at the timing at which the second condition is satisfied.

It is preferable that the image selection unit does not select the second image signal in a case where the blurring index values at any of the timings do not satisfy the second condition, and the computed image signal generation unit generates the computed image signal only on the basis of the first image signal. It is preferable that the image selection unit does not select the second image signal in a case where the blurring index values at any of the timings do not satisfy the second condition, and the computed image signal generation unit does not generate the computed image signal.

It is preferable that the endoscope system further comprises a warning display control unit that performs a control of displaying a warning in a case where the blurring index values at any of the timings do not satisfy the second condition. It is preferable that the endoscope system further comprises an information display control unit that performs a control of displaying an image based on the second image signals included in the multi-frame image signals at the first timing T1 and the specific timing, and the blurring index values at the first timing T1 and the specific timing on a display unit, and the image selection unit has an auto-selection mode where the second image signal that satisfy the second condition is automatically selected, and a manual selection mode where a second image signal selected and indicated by a user is selected among the second image signals displayed on the display unit, and performs image selection in either the auto-selection mode or the manual selection mode.

It is preferable that the image blurring amount is calculated on the basis of a blood vessel structure or a mucous membrane structure within the first image signal or the second image signal. It is preferable that the image blurring amount is calculated on the basis of a central region within the first image signal or the second image signal. It is preferable that a plurality of timings of a second timing T2 to an N-th timing TN are included in the specific timing (N represents an integer of 3 or more). It is preferable that the first illumination light and the second illumination light have different wavelength ranges, respectively.

A method of operating an endoscope system of the invention comprises sequentially generating first illumination light and second illumination light by a light source; sequentially imaging an observation object illuminated sequentially with the first illumination light and the second illumination light at a first timing T1, thereby outputting multi-frame image signals at the first timing T1 and sequentially images the observation object illuminated sequentially with the first illumination light and the second illumination light at a specific timing before the first timing T1, thereby outputting multi-frame image signals at the specific timing, by an imaging sensor; selecting a second image signal of which an image blurring amount satisfies a first condition from second image signals included in the multi-frame image signals at the first timing T1 and the specific timing, by an image selection unit; and performing computation based on a first image signal including in the multi-frame image signals at the first timing T1 and a second image signal selected in the image selection unit, thereby generating a computed image signal, by a computed image signal generation unit.

A method of operating an endoscope system of the invention comprises sequentially generating first illumination light and second illumination light by a light source; sequentially imaging an observation object illuminated sequentially with the first illumination light and the second illumination light at a first timing T1, thereby outputting multi-frame image signals at the first timing T1 and sequentially images the observation object illuminated sequentially with the first illumination light and the second illumination light at a specific timing before the first timing T1, thereby outputting multi-frame image signals at the specific timing, by an imaging sensor; calculating blurring index values at the first timing T1 and the specific timing on the basis of an image blurring amount of a first image signal and an image blurring amount of a second image signal in the multi-frame image signals at the first timing T1 and the specific timing, by a blurring index value calculation unit; selecting a second image signal at a timing at which the blurring index values satisfy a second condition among the second image signals included in the multi-frame image signals at the first timing T1 and the specific timing, by an image selection unit; and performing computation based on a first image signal included in the multi-frame image signals at the first timing T1 and a second image signal included in the multi-frame image signals selected in the image selection unit, thereby generating a computed image signal, by a computed image signal generation unit.

According to the invention, it is possible to accurately perform computation even in a situation where a blurred image is generated, in a case where various kinds of computation are performed on the basis of image signals at a plurality of timings obtained by radiating light having different wavelength ranges at different timings.

DESCRIPTION OF THE PREFERRED EMBODIMENTS

First Embodiment

Figure 1:
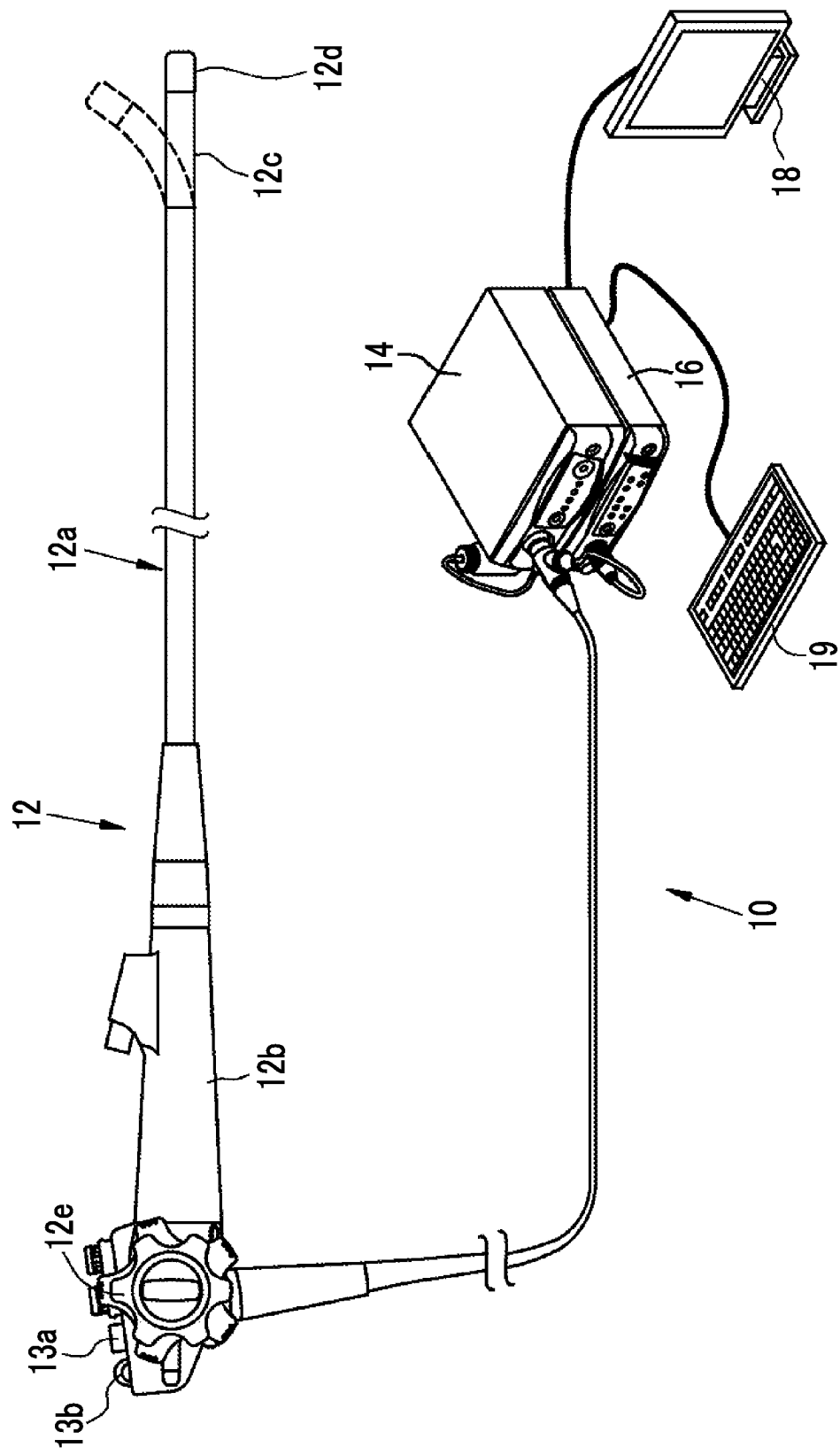
FIG. 1 is an external view of an endoscope system.

As illustrated in FIG. 1, an endoscope system 10 of a first embodiment has an endoscope 12, a light source device 14, a processor device 16, a monitor 18 (display unit), and a console 19. The endoscope 12 is optically connected to the light source device 14 and is electrically connected to the processor device 16. The endoscope 12 has an insertion part 12a to be inserted into a subject, an operating part 12b provided at a proximal end portion of the insertion part 12a, and a bending part 12c and a distal end part 12d provided on a distal end side of the insertion part 12a. By operating an angle knob 12e of the operating part 12b, the bending part 12c makes a bending motion. The distal end part is directed in a desired direction by this bending motion.

Additionally, the operating part 12b is provided with a mode changeover switch 13a, a zooming operating part 13b, an acquisition of the still image instruction part (not illustrated), and the like other than the angle knob 12e. The mode changeover switch 13a is used for switching the operation of observation modes. The endoscope system 10 has a normal observation mode and a special observation mode as the observation modes. In the normal observation mode, a natural-tone image (hereinafter, referred to as a normal image) obtained by imaging the observation object using white light for illumination light is displayed on the monitor 18. In the special observation mode, a specific depth blood vessel enhanced image obtained by extracting blood vessels at a specific depth among blood vessels included in the observation object, using image signals obtained by imaging the observation object, is displayed.

The processor device 16 is electrically connected to the monitor 18 and the console 19. The monitor 18 outputs and displays the image of the observation object, information accompanying the image of the observation object, and the like. The console 19 functions as a user interface that receives an input operation, such as a function setting. In addition, an external recording unit (not illustrated) that records the images, the image information, and the like may be connected to the processor device 16.

Figure 2:
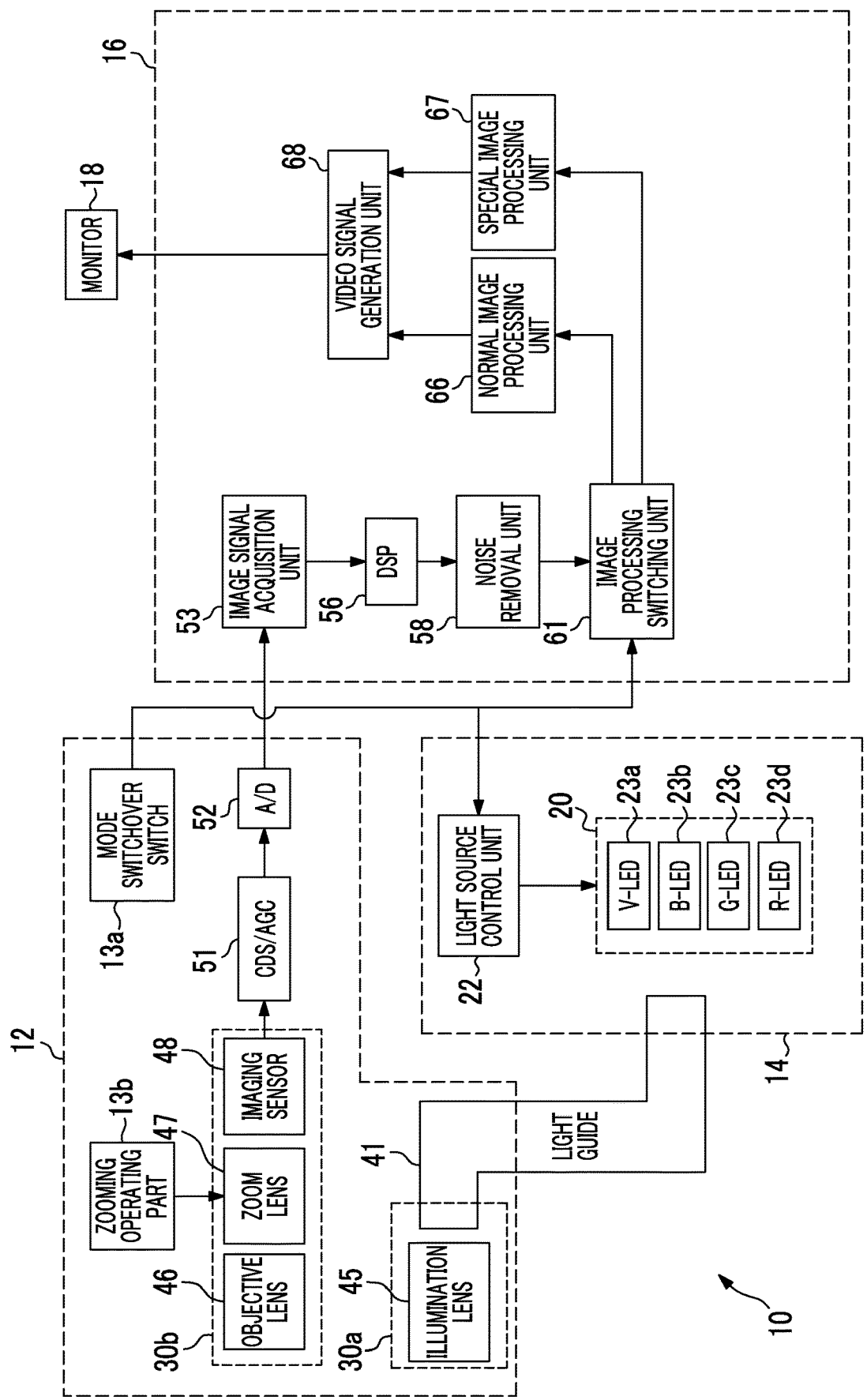
FIG. 2 is a block diagram illustrating the functions of the endoscope system.

As illustrated in FIG. 2, the light source device 14 includes a light source 20, and a light source control unit 22 that controls the light source 20. The light source 20 has, for example, a plurality of semiconductor light sources, turns on or off these semiconductor light sources, respectively, and generates illumination light for irradiating the observation object by controlling the light emission amounts of the respective semiconductor light sources in a case where the semiconductor light sources are turned on. In the present embodiment, the light source 20 has four color LEDs of a violet light emitting diode (V-LED) 23a, a blue light emitting diode (B-LED) 23b, a green light emitting diode (G-LED) 23c, and a red light emitting diode (R-LED) 23d.

Figure 3:
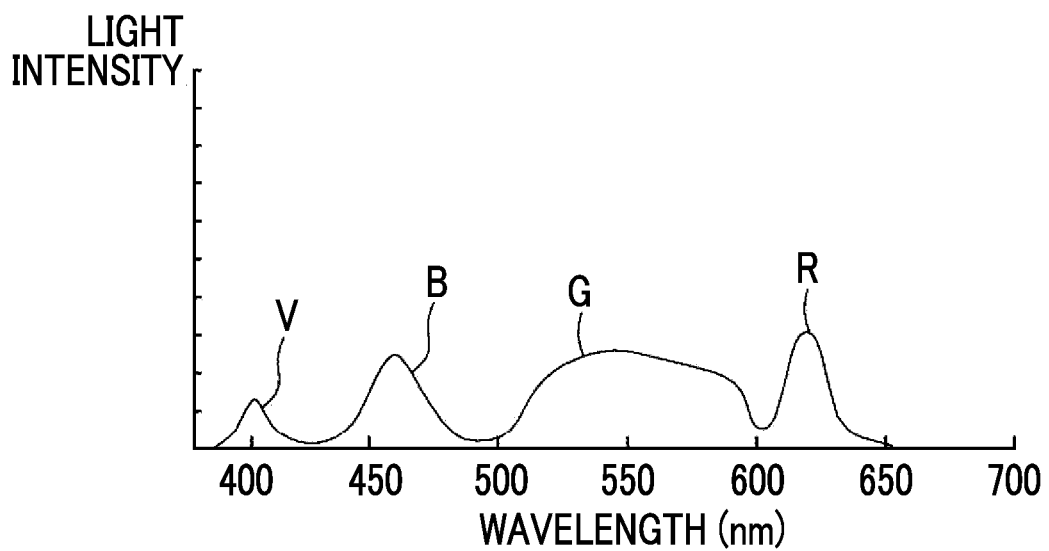
FIG. 3 is a graph illustrating the spectroscopic spectrum of purple light, blue light, green light, and red light.

As illustrated in FIG. 3, the V-LED 23a is a purple light source that emits purple light V having a central wavelength of 405 nm and a wavelength range of 380 to 420 nm. The B-LED 23b is a blue semiconductor light source that emits blue light B having a central wavelength of 460 nm and a wavelength range of 420 to 500 nm. The G-LED 23c is a green semiconductor light source that emits green light G having a wavelength range of 480 to 600 nm. The R-LED light source 23d is a red semiconductor light source that emits red light R having a central wavelength of 620 to 630 nm and a wavelength range of 600 to 650 nm. In addition, the central wavelengths of the V-LED 23a and the B-LED 23b have a width of about ±5 nm to ±10 nm. Additionally, in the respective LEDs 23a to 23d, the central wavelengths and peak wavelengths may be different from each other or may be the same as each other.

The light source control unit 22 can individually control ON/OFF states of the LEDs 23a to 23d, the light emission amounts thereof at the time of the ON state, and the like by inputting independent control signals to the LEDs, respectively. In the case of the normal observation mode, the light source control unit 22 turns on the V-LED 23a, the B-LED 23b, the G-LED 23c, and the R-LED 23d altogether. For this reason, in a normal observation mode, white light including the purple light V, the blue light B, the green light G, and the red light R is used as the illumination light.

On the other hand, in the case of the special observation mode, the light source control unit 22 controls the light source 20 so as to alternately perform a first light emission mode in which only the V-LED 23a is turned on and the other LEDs, such as the B-LED 23b, are turned off, and a second light emission mode in which the V-LED 23a is turned off, the B-LED 23b is turned on, and the other LEDs, such as the V-LED 23a, are turned off. That is, in the special observation mode, the purple light V and the blue light B are sequentially generated by performing the first light emission mode and the second light emission mode. In addition, the purple light V corresponds to "first illumination light", and the blue light B corresponds to "second illumination light" having a wavelength range different from the first illumination light.

In the present embodiment, as described above, in the special observation mode, the purple light V emitted from the V-LED 23a and the blue light B emitted from the B-LED 23b are used as they are as the first illumination light and the second illumination light. However, it is preferable that the respective wavelength ranges of the purple light V and the blue light B are further limited and then utilized as the illumination light in the special observation mode by providing the light source 20 with optical filters that limit wavelength ranges.

This is because, in a case where the first illumination light and the second illumination light are light of two wavelength ranges in which the scattering coefficients of the observation object are different from each other and the light absorption coefficients of hemoglobin are substantially equal to each other, the blood vessels at the specific depth can be particularly clearly extracted. For example, the scattering coefficients of the observation object in the wavelength ranges of the respective kinds of illumination light relate to the depths of reach to the observation object, that is, depths under mucous membranes of blood vessels observable in the wavelength ranges. Meanwhile, the light absorption coefficients of hemoglobin relate to the contrast of blood vessels observable with the respective kinds of illumination light. Hence, the conditions that the scattering coefficients of the observation object are different from each other and the light absorption coefficient of hemoglobin is substantially equal to each other, which are required of the first illumination light and the second illumination light to be used in the special observation mode, are conditions that light of two wavelength ranges in which the depths under the mucous membranes of the observable blood vessels are different from each other and blood vessels having different depths under the mucous membranes are observable with the same degree of contrast is selected and used.

There is a case where the above conditions are not completely satisfied depending on characteristics (central wavelengths) of LEDs or the like to be used for the light source 20. However, in such a case, light of two wavelength ranges in which the light absorption coefficient of hemoglobin are as close as possible at least within a range where the scattering coefficients of the observation object are different from each other may be set as the first illumination light and the second illumination light. In addition, supposing the first illumination light is light of a wavelength range shorter than the second illumination light, the expression "the scattering coefficients of the observation object are different from each other" means that the ratio of the scattering coefficients of the second illumination light to the scattering coefficient of the first illumination light is 0.8 or less. Additionally, a difference between the scattering coefficient of the first illumination light and the second illumination light hopes that there may be 70 $cm^{-1}$ or more.

Figure 4:
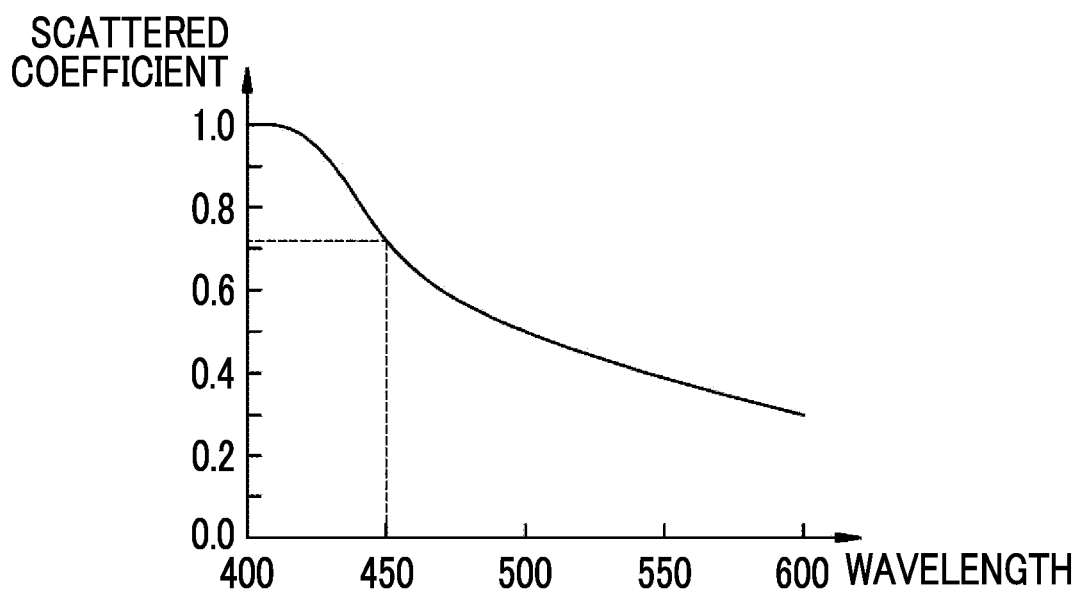
FIG. 4 is a graph illustrating a scattering coefficient of an observation object.
Figure 5:
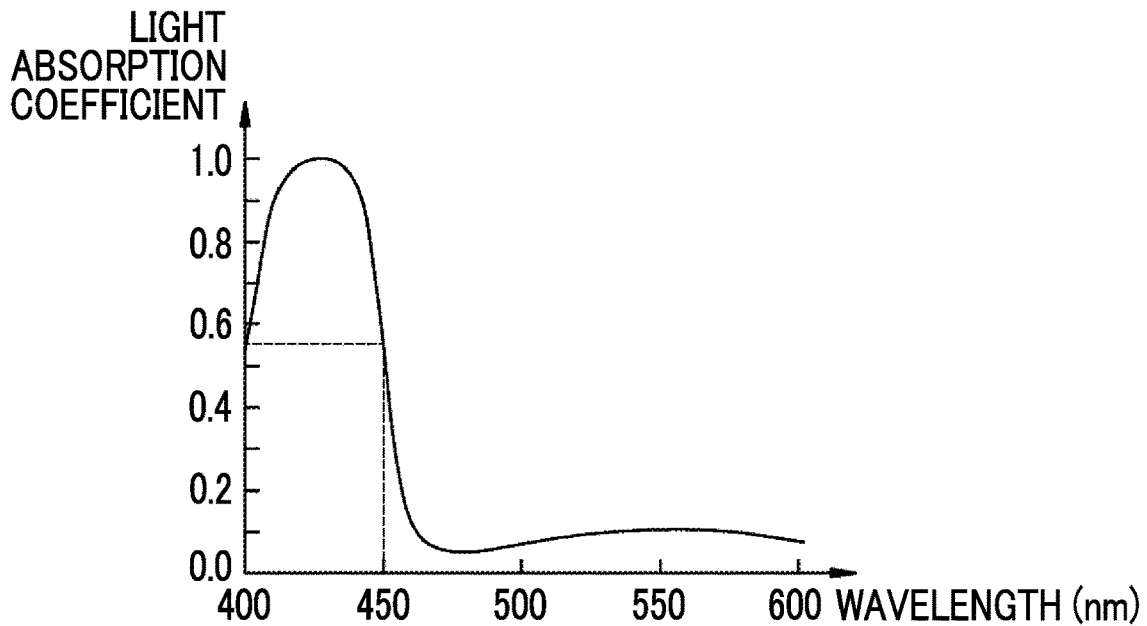
FIG. 5 is a graph illustrating a light absorption coefficient of hemoglobin.

With the purple light V and the blue light B to be used as illumination light in the special observation mode, as illustrated in FIG. 4, the ratio of the scattering coefficient of the blue light B to the scattering coefficient of the purple light V is 0.75. Additionally, as illustrated in FIG. 5, the light absorption coefficients (Light absorption coefficient of oxygenated hemoglobin:Light absorption coefficient of reduced hemoglobin=3:7) of hemoglobin is approximately equal to each other.

As illustrated in FIG. 2, light of respective colors emitted from the respective LEDs 23a to 23d enters a light guide 41 inserted into the insertion part 12a via a light path coupling part (not illustrated) formed with a mirror, a lens, or the like. The light guide 41 is built in the endoscope 12 and a universal cord (a cord that connects the endoscope 12, and the light source device 14 and the processor device 16 together). The light guide 41 propagates the illumination light generated by the light source 20 up to the distal end part 12d of the endoscope 12.

The distal end part 12d of the endoscope 12 is provided with an illumination optical system 30a and an imaging optical system 30b. The illumination optical system 30a has an illumination lens 45, and the illumination light propagated by the light guide 41 is radiated to the observation object via the illumination lens 45. The imaging optical system 30b has an objective lens 46, a zoom lens 47, and an imaging sensor 48. Various kinds of light, such as reflected light, scattered light, and fluorescence from the observation object resulting from radiating illumination light, enters the imaging sensor 48 via the objective lens 46 and the zoom lens 47. Accordingly, the image of the observation object is formed on the imaging sensor 48. The zoom lens 47 is freely moved between a telephoto end and a wide end by operating the zooming operating part 13b, and magnifies or reduces a reflected image of the observation object of which the image is to be formed on the imaging sensor 48.

Figure 6:
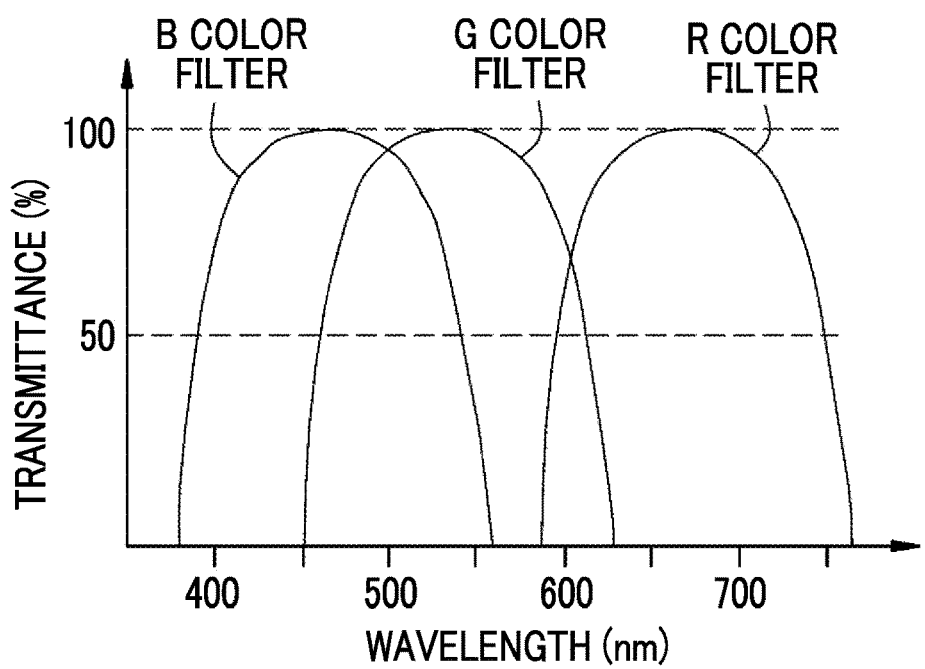
FIG. 6 is a graph illustrating spectral characteristics of color filters.

The imaging sensor 48 is a color imaging sensor, and the imaging sensor 48 includes a R pixel (red pixel) provided with an R (red) color filter, a G pixel (green pixel) provided with a G (green) color filter, and a B pixel (blue pixel) provided with a B (blue) color filter. As illustrated in FIG. 6, the R color filter transmits light of 580 770 nm, the G color filter transmits light of 450 to 630 nm, and the B color filter transmits light of 380 to 560 nm.

The imaging sensor 48 outputs image signals in respective RGB colors from pixels in respective colors in accordance with emission of the illumination light. In the normal observation mode, the imaging sensor 48 images the observation object illuminated with the white light, thereby outputs an Rc image signal from the R pixel, outputs a Gc image signal from the G pixel, and outputs a Bc image signal from the B pixel. In the special observation mode, in a case where the purple light V is emitted in the first light emission mode, the imaging sensor 48 images the observation object illuminated with the purple light V, thereby outputting an R1 image signal from the R pixel, outputs a G1 image signal from the G pixel, and outputs a B1 image signal from the B pixel. A signal of a wavelength component corresponding to the purple light V is included in the B1 image signal (corresponding to a "first image signal").

Additionally, in a case where the blue light B is emitted in the second light emission mode, the imaging sensor 48 images the observation object illuminated with the blue light B thereby outputting an R2 image signal from the R pixel, outputs a G2 image signal from the G pixel, and outputs a B2 image signal from the B pixel. A signal of a wavelength component corresponding to the blue light B is included in the B2 image signal (corresponding to a "second image signal").

The plurality of image signals including the B1 image signal and the B2 image signal obtained by performing the first light emission mode and the second light emission mode as described above are hereinafter referred to as multi-frame image signals.

As the imaging sensor 48, a charge coupled device (CCD) imaging sensor or a complementary metal-oxide semiconductor (CMOS) imaging sensor is available. Additionally, instead of the primary color imaging sensor 48, a complementary color imaging sensor including complementary color filters in C (cyan), M (magenta), Y (yellow), and G (green) may be used. In a case where the complementary color imaging sensor is used, image signals in four colors of CMYG are output. Thus, image signals of RGB that are the same colors as those of the imaging sensor 48 can be obtained by converting the image signals in four colors of CMYG into the image signals in three colors of RGB through color conversion of complementary color to primary color. Additionally, instead of the imaging sensor 48, a monochrome sensor that is not provided with the color filters may be used.

The CDS/AGC circuit 51 performs correlation double sampling (CDS) and automatic gain control (AGC) on analog image signals obtained from the imaging sensor 48. The image signals that have passed through the CDS/AGC circuit 51 are converted into digital image signals by an analog-to-digital (A/D) converter 52. The digital image signals after the A/D conversion are input to the processor device 16.

As illustrated in FIG. 2, the processor device 16 includes an image signal acquisition unit 53, a digital signal processor (DSP) 56, a noise removal unit 58, an image processing switching unit 61, a normal image processing unit 66, a special image processing unit 67, and a video signal generation unit 68. The image signal acquisition unit 53 acquires digital image signals from the imaging sensor 48 via the CDS/AGC circuit 51 and an A/D converter 52. For example, the processor device 16 has a central processing unit (CPU), and the CPU functions as the image signal acquisition unit 53, the noise removal unit 58, the image processing switching unit 61, the normal image processing unit 66, the special image processing unit 67, and the video signal generation unit 68.

The DSP 56 performs various kinds of signal processing, such as defect correction processing, offset processing, gain correction processing, linear matrix processing, gamma conversion processing, demosaicing processing, and the like, on the acquired image signals. In the defect correction processing, a signal of a defective pixel of the imaging sensor 48 is corrected. In the offset processing, a dark current component is removed from image signals subjected to the defect correction processing, and an accurate zero level is set. In the gain correction processing, a signal level is adjusted by multiplying the image signals after the offset processing by a specific gain.

The linear matrix processing for enhancing color reproducibility is performed on the image signals after the gain correction processing. Then, brightness and color saturation are adjusted by the gamma conversion processing. The demosaicing processing (also referred to as equalization processing of a grade or synchronization processing) is performed on the image signals after the gamma conversion processing, and a signal of a color that runs short in each pixel is generated by interpolation. By means of this demosaicing processing, all pixels have signals of respective RGB colors. The noise removal unit 58 performs noise removal processing using (for example, a moving average method, a median filter method, or the like) on the image signals subjected to the demosaicing processing or the like by the DSP 56, and removes noise. The image signals from which noise are removed is transmitted to the image processing switching unit 61. The image processing switching unit 61 transmits the received image signals to the normal image processing unit 66 in a case where the normal observation mode is set by the operation of the mode changeover switch 13a, and transmits the received image signals to the special image processing unit 67 in a case where the special observation mode is set.

The normal image processing unit 66 operates in a case where the normal observation mode is set, and performs color conversion processing, color enhancement processing, and structure enhancement processing on the received image signals to generate normal image signals. In the color conversion processing, color conversion processing is performed on the RGB image signals by 3×3 matrix processing, gradation transformation processing, three-dimensional look-up table (LUT) processing, and the like. The color enhancement processing is performed on the image signals subjected to the color conversion processing. The structure enhancement processing is, for example, the processing of enhancing the structure of the observation object, such as surface layer blood vessels and pit patterns, and is performed on the image signals after the color enhancement processing. As described above, a color image obtained using the normal image signals subjected to the various kinds of image processing and the like up to the structure enhancement processing is a normal image.

Figure 7:
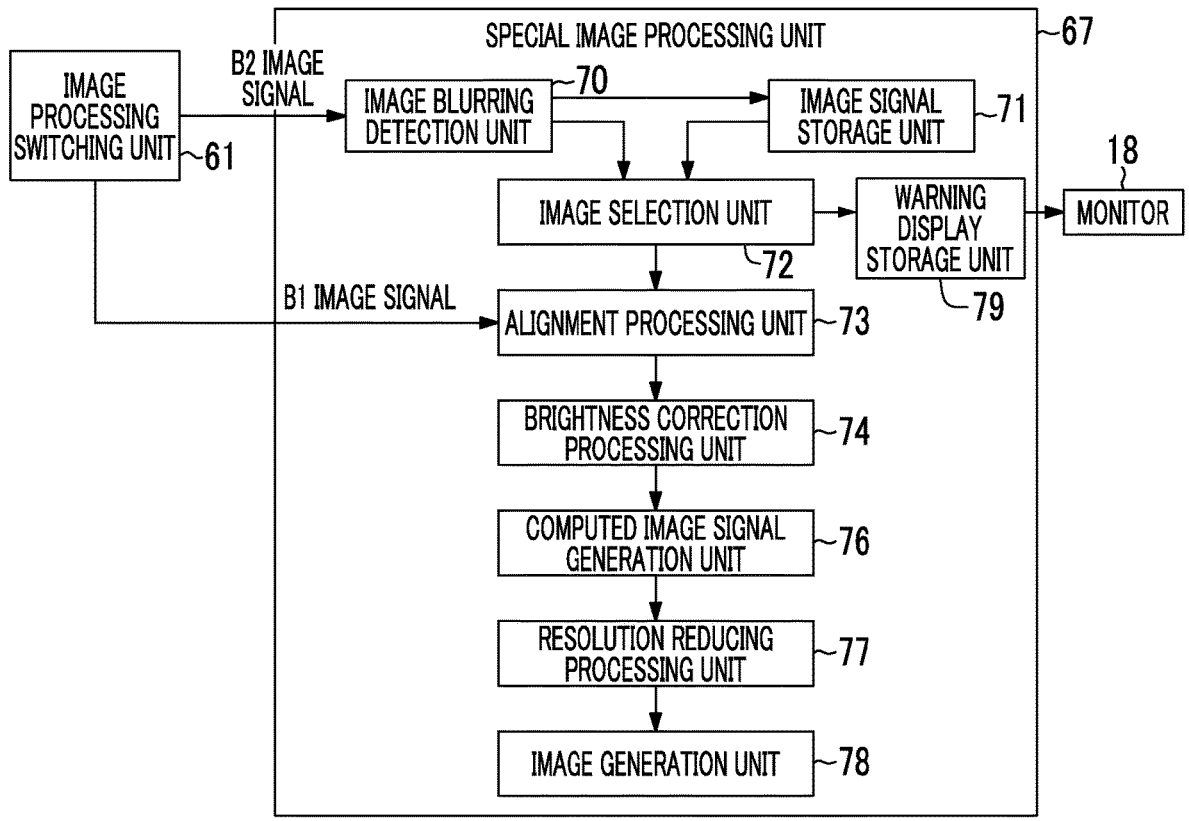
FIG. 7 is a block diagram illustrating the functions of a special image processing unit of a first embodiment.

The special image processing unit 67 is an image processing unit that operates in a case where the special observation mode is set, extracts the blood vessels at the specific depth using the multi-frame image signals including the B1 image signal and the B2 image signal, and generates an image representing the extracted blood vessels by color differences with respect to other blood vessels. As illustrated in FIG. 7, the special image processing unit 67 includes an image blurring detection unit 70, an image signal storage unit 71, an image selection unit 72, an alignment processing unit 73, a brightness correction processing unit 74, an computed image signal generation unit 76, a resolution reduction processing unit 77, an image generation unit 78, and a warning display control unit 79. Among the multi-frame image signals input from the image processing switching unit 61, the B1 image signal is input to the alignment processing unit 73, and the B2 image signal is input to the image blurring detection unit 70.

The image blurring detection unit 70 detects the image blurring amount of the input B2 image signal. It is preferable that the image blurring amount is a vector quantity having the direction and the magnitude of blurring of an image. The detected image blurring amount is associated with the B2 image signal and stored in the image signal storage unit 71. Additionally, the B2 image signal associated with the image blurring amount is transmitted to the image selection unit 72. Here, as the image blurring amount, it is preferable to detect the image blurring amount of a structure of interest in the B2 image signal. For example, as the structure of interest, there is a blood vessel structure or a mucous membrane structure. In the present embodiment, since the structure of interest is a blood vessel, it is preferable to calculate the image blurring amount on the basis of the blood vessel structure. For example, it is preferable to specify a blood vessel position by an image filter that extracts the blood vessel structure, and set the image blurring amount of a blood vessel at this specified blood vessel position as a representative value of the image blurring amount of the entire image, that is, an image blurring amount to be adopted in the image blurring detection unit 70.

Additionally, it is preferable the image blurring amount is calculated on the basis of a central image region of the B2 image signal. It is preferable that the central image region is arbitrarily determined as "the middle of an image that is vertically and horizontally into three" or "a region within pixels having a radius Rd from a central point of an image". In addition, the reason why the image blurring amount of the central image region is adopted in this way is because a user is operating the endoscope 12 such that a region of interest is located at the center of the image.

In addition, as methods for detecting the image blurring amount, mainly, there are a method based on image analysis, and a method based on the imaging sensor 48. As the method based on image analysis, there is a method of estimating a point spread function (PSF) estimated regarding each of a plurality of regions set in an image, and estimating the direction and the magnitude of image blurring with high accuracy from the point spread function (refer to Japanese Patent No. 5499050). Additionally, it is known that a blurred image, which is generated in a case where the endoscope 12 is linearly operated even in the image blurring, appears as a power spectrum in which a sink function is convolved in a frequency space. Under circumstances in which such blurred images are frequently generated, it is preferable to convert image signals into an image of a frequency domain, and detect the image blurring amount on the basis of the degree of the influence of a sink function that appears in a direction of blurring in the image of the frequency domain (refer to JP2009-230598A). Additionally, there is a method of detecting a movement vector from an image signal and detecting the image blurring amount on the basis of the movement vector (refer to JP1991-16470 (JP-H03-16470)).

Meanwhile, as the method based on the imaging sensor 48, there is a method of detecting angular velocity and a movement direction using movement distance detecting means provided in the bending part 12c of the endoscope 12 and detecting the image blurring amount from the angular velocity and the movement direction (JP1993-16470 (JP-H05-16470)).

Figure 8:
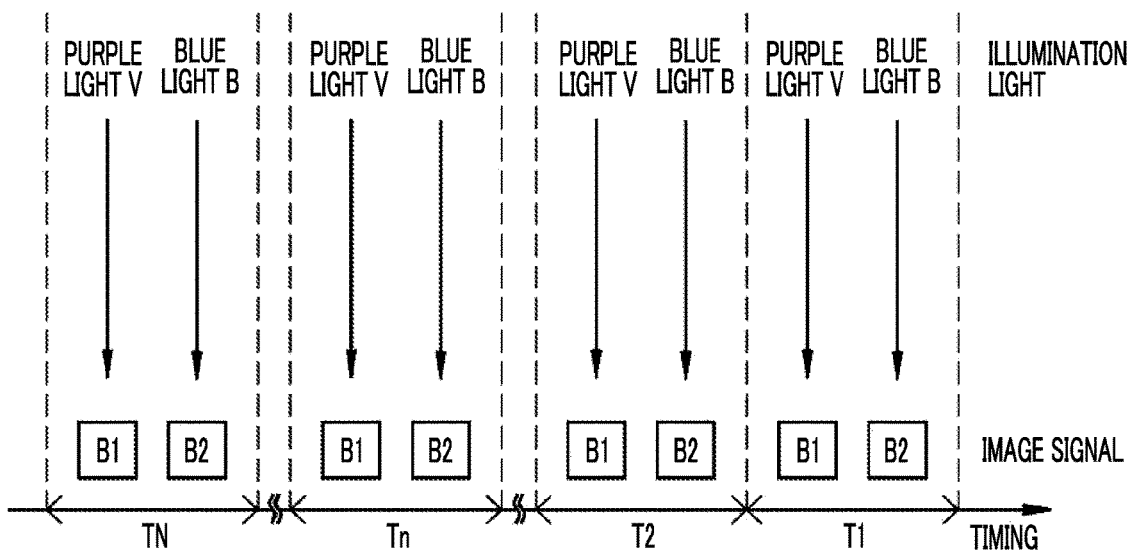
FIG. 8 is an illustrative view illustrating a B1 image signal and a B2 image signal that are obtained in a case where purple light V and blue light B are emitted at a first timing T1 to an N-th timing TN, respectively.

The image selection unit 72 selects the B2 image signal with less image blurring from the B2 image signal input from the image blurring detection unit 70 or the B2 image signal stored in the image signal storage unit 71. The selected B2 image signal is input to the alignment processing unit 73. Specifically, as illustrated in FIG. 8, the image selection unit 72 performs selection out of the B2 image signal among the multi-frame image signals obtained in a case where emission of the purple light V and the blue light B is performed at the first timing T1, and the B2 image signal of the multi-frame image signals obtained in a case where emission of the purple light V and the blue light B is performed at a plurality of a second timing T2, . . . , an n-th timing, . . . , and an N-th timing TN earlier than the first timing T1.

The B2 image signal at the first timing T1 is a signal input to the image selection unit 72 without going through the image signal storage unit 71. The B2 image signals at the second timing T2, . . . , the n-th timing, . . . , and the N-th timing TN are signals input to the image selection unit 72 via the image signal storage unit 71. In addition, in FIG. 8, "B1" represents the B1 image signal and "B2" represents the B2 image signal. Additionally, in the invention, the plurality of timings earlier than the first timing T1 or are generically referred to as "specific timings". In the present embodiment, the second timing T2 to the N-th timing TN are equivalent to the "specific timings".

Here, n and N are natural numbers equal to or greater than 2, and n is an arbitrary natural number in 2 to N. The second timing T2 is closest to the first timing T1 in time, and is separated from the first timing T1 in time as "n" of the n-th timing Tn becomes greater, and the N-th timing TN is most separated from the first timing T1 in time. Additionally, the first timing T1 includes both a timing at which the purple light V is emitted in the first light emission mode and the B1 image signal is obtained, and a timing at which the blue light B is emitted in the second light emission mode and the B2 image signal is obtained. The second timing T2 to the N-th timing TN also include the timing at which the B1 image signal is obtained, and the timing at which the B2 image signal is obtained, similarly to the first timing.

In the image selection unit 72, first, it is determined whether or not the image blurring amount of the B2 image signal at the first timing T1 exceeds a threshold value Th1. In a case where the image blurring amount is lower than the threshold value Th1 as a result of the determination, the B2 image signal at the first timing T1 is transmitted to the alignment processing unit 73. In contrast, in a case where the image blurring amount exceeds the threshold value Th1, it is determined whether or not the image blurring amount of the B2 image signal at the second timing T2 exceeds Th1. As a result of the determination, in a case where the image blurring amount is lower than the threshold value Th1, the B2 image signal at the second timing T2 is transmitted to the alignment processing unit 73, and in a case where the image blurring amount exceeds the threshold value Th1, the image blurring amount of the B2 image signal at the third timing T3, is determined and it is determined whether the image blurring amount should be transmitted to the alignment processing unit 73. The image selection unit 72 performs the same determination as above until the image blurring amount of which the B2 image signal is lower than the threshold value Th1 is detected. In addition, a "first condition" corresponds to "the image blurring amount is lower than the predetermined threshold value Th1 and imaging is performed at a timing closest to the first timing T1".

In addition, in the image selection unit 72, a positional deviation from the B1 image signal frequently becomes large regarding the B2 image signals at timings excessively separated from the first timing T1 in time. For this reason, it is preferable to select the B2 image signal in which the image blurring amount falls below the threshold value Th1 and the timing is closest to the first timing T1 in time. Additionally, in a case where all image blurring amounts of the B2 image signals at the second timing T2 to the N-th timing TN exceed the threshold value Th1, it is preferable that the image selection unit 72 does not select the B2 image signals at any of the timings.

In this way, in a case where all the image blurring amounts of the B2 image signals at the second timing T2 to the N-th timing TN exceed the threshold value Th1, it is preferable that the computed image signal generation unit 76 generates computed image signals only on the basis of the B1 image signals or does not generate computed image signals. Additionally, in a case where all the image blurring amounts of the B2 image signals at the second timing T2 to the N-th timing TN exceed the threshold value Th1, it is preferable that the warning display control unit 79 displays a warning display on the monitor 18 by performing the control of performing the warning display. There are a warning message, a warning mark, and the like as the warning display.

The alignment processing unit 73 performs alignment between the observation object represented by the B1 image signal and the observation object represented by the B2 image signal, which are sequentially acquired. The alignment processing unit 73 corrects at least one of the B1 image signal or the B2 image signal.

The brightness correction processing unit 74 corrects the brightness of at least one of the B1 image signal or the B2 image signal such that the brightnesses of the B1 image signal and the B2 image signal aligned by the alignment processing unit 73 have a specific ratio. Specifically, since the light quantity ratio of the purple light V in the first light emission mode and the blue light B in the second light emission mode is known, gain correction is performed such that the brightness of the B1 image signal is made to coincide with the brightness of the B2 image signal in order to obtain brightnesses in a case where the observation object is irradiated with the purple light V and the blue light B of respectively equal light quantities, using the light quantity ratio.

In addition, in a case where the B2 image signals at any the timings T1- to TN are not selected by the image selection unit 72, the alignment is not performed in the alignment processing unit 73, and the correction of the brightness is not performed in the brightness correction processing unit 74. That is, only the B1 image signal is sent to the computed image signal generation unit 76.

The computed image signal generation unit 76 performs computation using the B1 image signal and the B2 image signal, and generates a computed image signal. Specifically, the difference or ratio of the B1 image signal and the B2 image signal is calculated. In the present embodiment, the computed image signal generation unit 76 log transforms the B1 image signal and the B2 image signal, and generates a difference between the B1 image signal and the B2 image signal after the logarithmic transformation, more specifically, and a computed image signal $\Delta B$ obtained by subtracting the B1 image signal from the B2 image signal. In a case where the B1 image signal and the B2 image signal are used as they are without being log transformed, the computed image signal is generated by computing the ratio of the B1 image signal and the B2 image signal for each pixel. The B1 image signal and the B2 image signal have pixel values proportional to densities in a case where these signals are log transformed, although respective pixels have pixel values proportional to received light quantities. Thus, stable computation results can be obtained irrespective of the illuminance of illumination light in a case where respective image signals are obtained.

Figure 9:
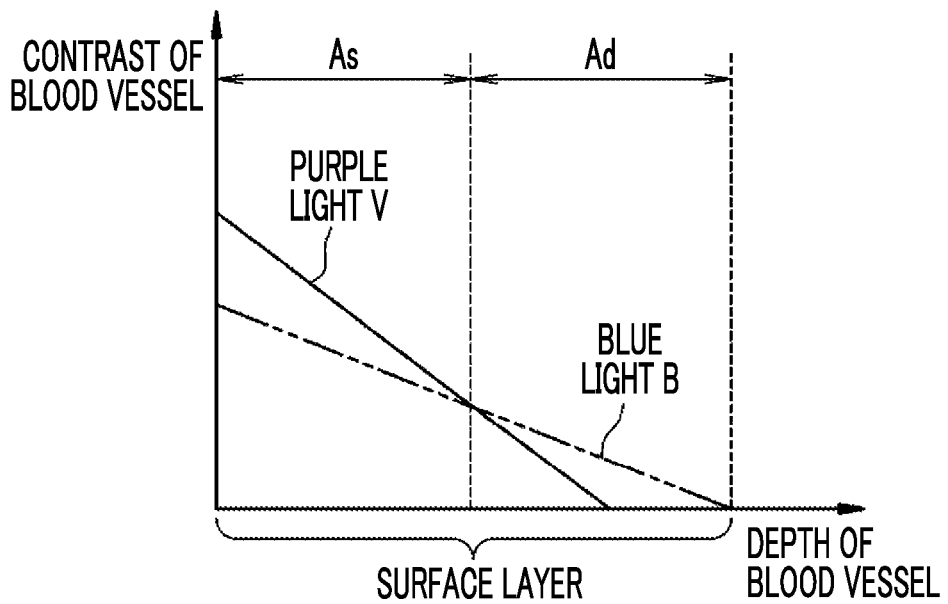
FIG. 9 is a graph schematically expressing a relationship between the depth of a blood vessel and the contrast of the blood vessel.

Calculating the computed image signal $\Delta B$ corresponds to extracting blood vessels at a specific depth under a mucous membrane. For example, as illustrated in FIG. 9, in a case where the purple light V and the blue light B are used as the illumination light, it is possible to observe approximately surface layer blood vessels (blood vessels within the total range of depth As and depth Ad). Since the purple light V has a wavelength shorter than the blue light B, the degree of penetration to the observation object is low, and only blood vessels at the position As that is relatively shallow under the mucous membrane with respect to the blue light B are imaged. Instead, in the purple light V, the contrast (the ratio of the quantity of reflected light from a surrounding mucous membrane to the quantity of reflected light from blood vessels) of the blood vessels at the shallow position As is larger than that in a case where the blue light B is used.

Meanwhile, since the blue light B has a wavelength longer than the purple light V, the degree of penetration to the observation object is high, and even blood vessels at the position Ad that is relatively deep under the mucous membrane with respect to the purple light V are imaged. Instead, in the blue light B, the contrast of the blood vessels at the shallow position As is smaller than that in a case where the purple light V is used. For this reason, in a case where the B1 image signal corresponding to the purple light V is subtracted from the B2 image signal corresponding to the blue light B, the pixel values of pixels representing particularly extreme surface layer blood vessels at a shallow position As under the mucous membrane are enhanced and become large values (white). On the contrary, the pixel values of pixels representing the surface layer blood vessels at the position Ad deeper than the extreme surface layer blood vessels become small values (black).

Additionally, in the computed image signal generation unit 76, computation is performed on the basis of the B2 image signal with less image blurring selected by the image selection unit 72, it is possible to generate the computed image signal $\Delta B$ obtained by substantially accurately extracting the blood vessels on the observation object.

The resolution reduction processing unit 77 is a so-called low-pass filter (hereinafter referred to as LPF), and reduces the resolution the computed image signal $\Delta B$ generated by the computed image signal generation unit 76. The intensity of the resolution reduction processing that the resolution reduction processing unit 77 performs on the computed image signal $\Delta B$ is determined by the cut-off frequency of the LPF. The cut-off frequency of the LPF is set in advance, and the resolution of the computed image signal is lower than at least the resolution of an original computed image signal ΔB.

The image generation unit 78 generates an image having a plurality of output channels, using either the B1 image signal or the B2 image signal received by the special image processing unit 67 and the resolution-reduced computed image signal ΔB. More specifically, the image generation unit 78 generates an image having a luminance channel Y and two color difference channels Cb and Cr related to color differences. The image generation unit 78 allocating either the B1 image signal or the B2 image signal to the luminance channel Y and allocates the resolution-reduced computed image signal ΔB to the two color difference channels Cb and Cr, thereby generating an image (hereinafter a specific depth blood vessel enhanced image) in which a traveling pattern of the blood vessels at the specific depth is enhanced in colors. Here, since the computed image signal ΔB allocated to the two color difference channels Cb and Cr is a signal obtained by substantially accurately extracting the blood vessels on the observation object, there is no concern that artifacts, such that colors equivalent to the blood vessels are displayed on a portion with no blood vessel, may be generated.

Figure 10:
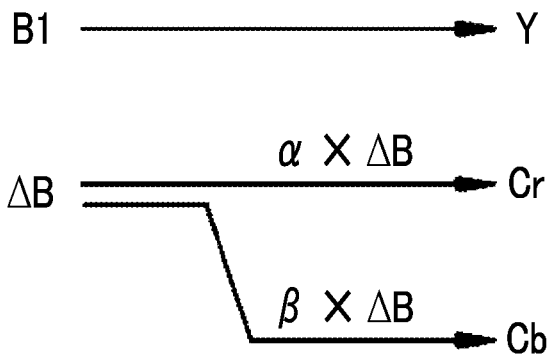
FIG. 10 is an illustrative view illustrating a method of generating a specific depth blood vessel enhanced image.

In addition, in the case of the present embodiment, the reason why the B1 image signal is allocated to the luminance channel Y is because the extreme surface layer blood vessels are selectively enhanced from the surface layer blood vessels. As illustrated in FIG. 10, the B1 image signal which corresponds to light (purple light V) of a relatively short wavelength range out of the B1 image signal and the B2 image signal and in which the contrast of the surface layer blood vessels is high is allocated to the luminance channel Y. Also, the computed image signal ΔB is allocated to the color difference channels Cb and Cr. Additionally, in a case where the computed image signal ΔB is allocated to the color difference channels Cb and Cr, multiplication is made by a coefficient α and a coefficient β, respectively. This is for aligning an image and tone to be displayed by an endoscope system that enhances and observes the surface layer blood vessels or the like.

Specifically, in related-arts endoscope system that enhance and observe surface layer blood vessels, in the case of an enhancement observation mode, narrow-band blue light is radiated to image an observation object to acquire a B image signal, and narrow-band green light is radiated to image the observation object to acquire a G image signal. Then, by allocating the B image signal to a B channel (blue channel) and a G channel (green channel) of an display image and allocating a G image signal to an R channel (red channel), middle-depth blood vessels at a deep position under a mucous membrane are turned into colors of a green system (cyan system), and surface layer blood vessels at a shallow position under the mucous membrane are turned into colors of a red system (magenta system) and are enhanced and displayed. In ITU-R.601, a relationship between the respective RGB image signals, the luminance channel Y, and the color difference channels Cb and Cr is expressed by the following Equation (1), (2), and (3).

$$Y=0.299R+0.587G+0.114B \tag{1}$$

$$Cb=-0.169R-0.331G+0.5B \tag{2}$$

$$Cr=0.5R-0.419G-0.081B \tag{3}$$

Then, in Equation (2) and Equation (3) of the color difference channels Cb and Cr, in a case where G is substituted for R and B is substituted for G, the color difference channels Cb and Cr can be expressed with (G−B) as shown in Equation (4) and Equation (5).

$$Cb=-0.169G+0.169B=0.169(G-B) \tag{4}$$

$$Cr=0.5G-0.5B=0.5(G-B) \tag{5}$$

In the present embodiment, since the extreme surface layer blood vessels are extracted and displayed, the computed image signal ΔB is used instead of this (G−B) signal. That is, multiplication by a coefficient α=0.169 to allocate the computed image signal ΔB to a color-difference signal Cb, and multiplication is made by the coefficient β=0.5 to allocate the computed image signal ΔB to a color-difference signal Cr. Accordingly, an image of substantially the same color scheme as the related-art endoscope systems is displayed in the endoscope system 10. Here, in order to enhance differences in color between the extreme surface layer blood vessels and the surface layer blood vessels at the relatively deep position, there is a case where the above coefficient α and the above coefficient β may be further multiplied by coefficients in accordance with settings or the like.

In addition, in order to generate the specific depth blood vessel enhanced image of RGB from the luminance channel Y and the color difference channels Cb and Cr, the followings are performed in accordance with the inverse transformation of ITU-R.601.

$$R=Y+1.402Cr \tag{7}$$

$$G=Y-0.344Cb-0.714Cr \tag{8}$$

$$B=Y+1.772Cb \tag{9}$$

The normal image generated by the normal image processing unit 66, and the specific depth blood vessel enhanced image generated by the special image processing unit 67 are input to the video signal generation unit 68. The video signal generation unit 68 converts the normal image and the specific depth blood vessel enhanced image into video signals for display as an image that can be displayed by the monitor 18. The monitor 18 displays the normal image and the specific depth blood vessel enhanced image using the video signals.

Figure 11:
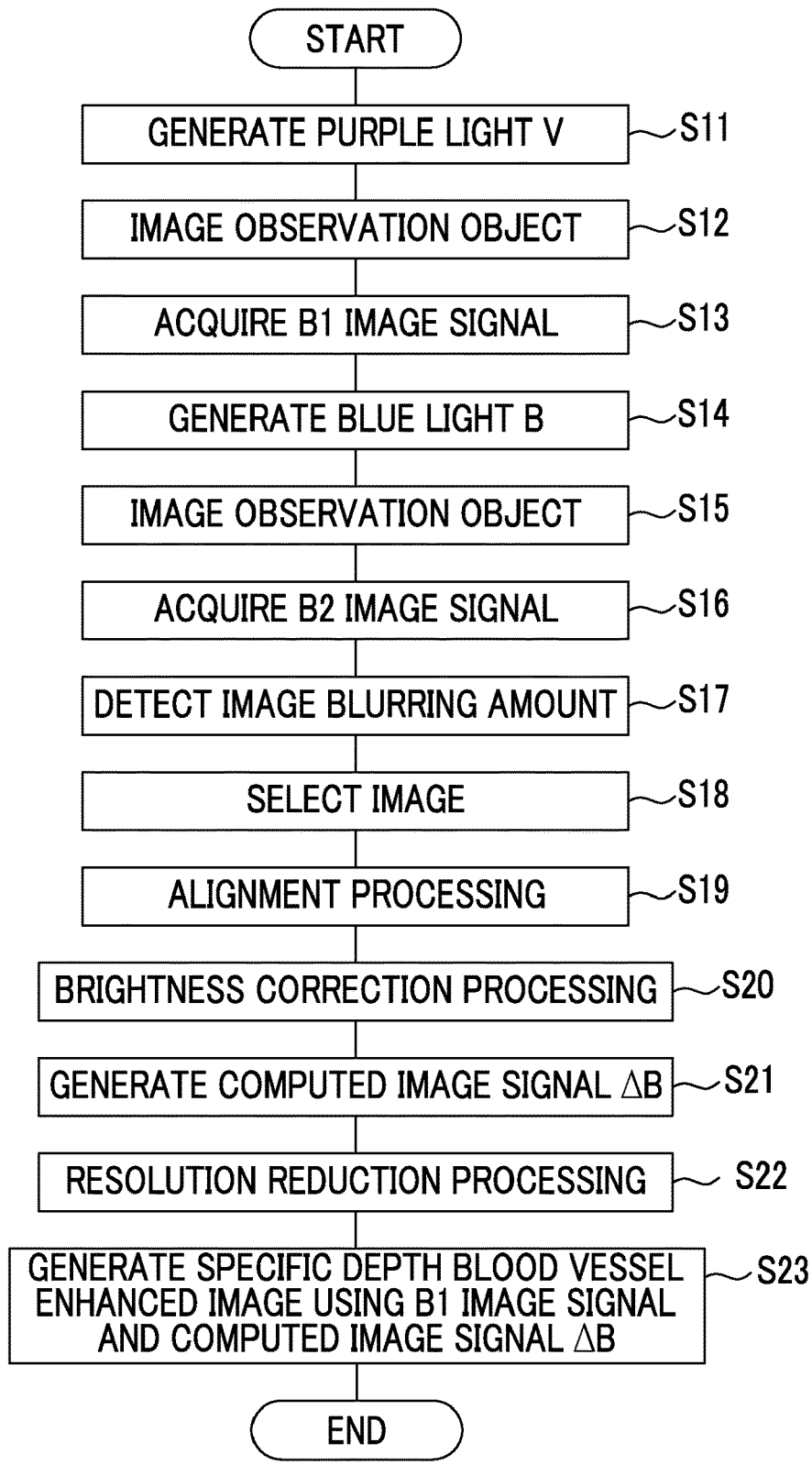
FIG. 11 is a flowchart in a special observation mode.

Next, a series of flow of the image processing in the special observation mode will be described with reference to FIG. 11. In a first step of the series of flow of the image processing illustrated in FIG. 11, it is premised that image blurring amounts corresponding to the B2 image signal at the second timing T2 to the N-th timing TN are already stored in the image signal storage unit 71.

Figure 12:
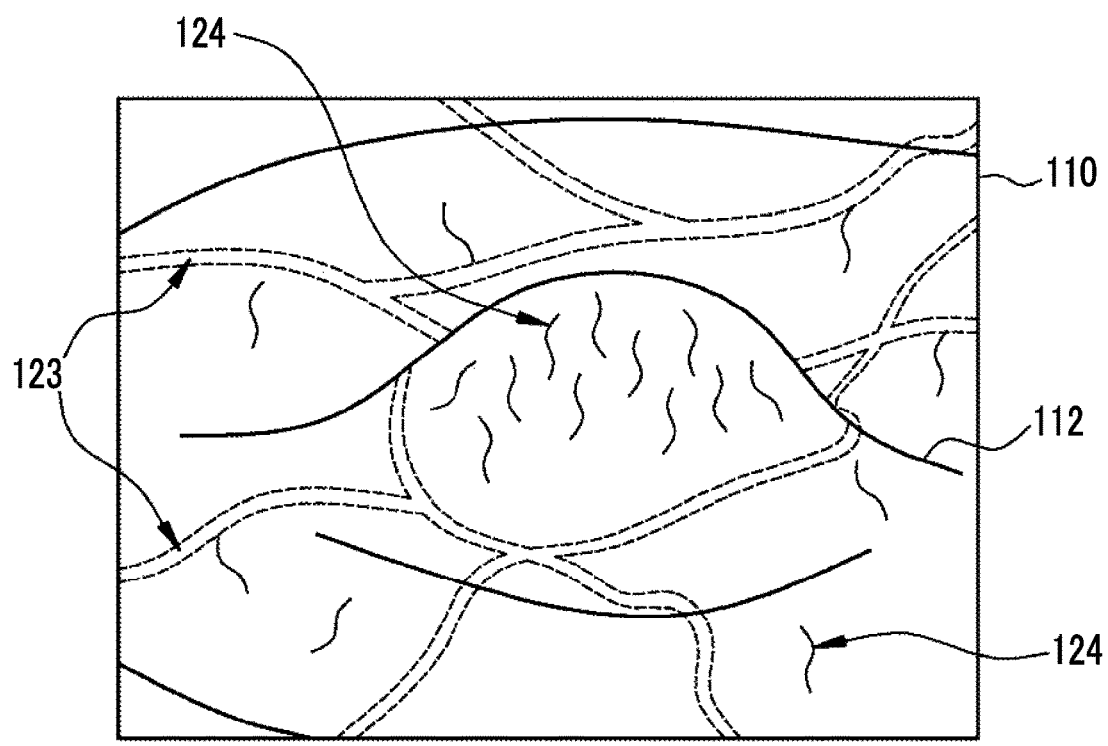
FIG. 12 is a schematic view of a B1 image signal.

First, the first light emission mode and the second light emission mode are performed at the first timing T1. In the first light emission mode, the light source 20 generates the purple light V, and irradiates the observation object with the generated purple light V (S11). The imaging sensor 48 images the observation object irradiated with the purple light V (S12), and the image signal acquisition unit 53 acquires the B1 image signal corresponding to the purple light V (S13). As illustrated in FIG. 12, since a B1 image signal 110 is an image signal obtained by imaging the observation object with the purple light V, it is possible to observe extreme surface layer blood vessels 124 in addition to shapes 112, such as ups and downs of the observation object. Additionally, surface layer blood vessels 123 at a position deeper under a mucous membrane than the extreme surface layer blood vessels 124 can be observed with the B1 image signal 110. The B1 image signal at the above first timing is transmitted to the alignment processing unit 73 via various processing units.

Figure 13:
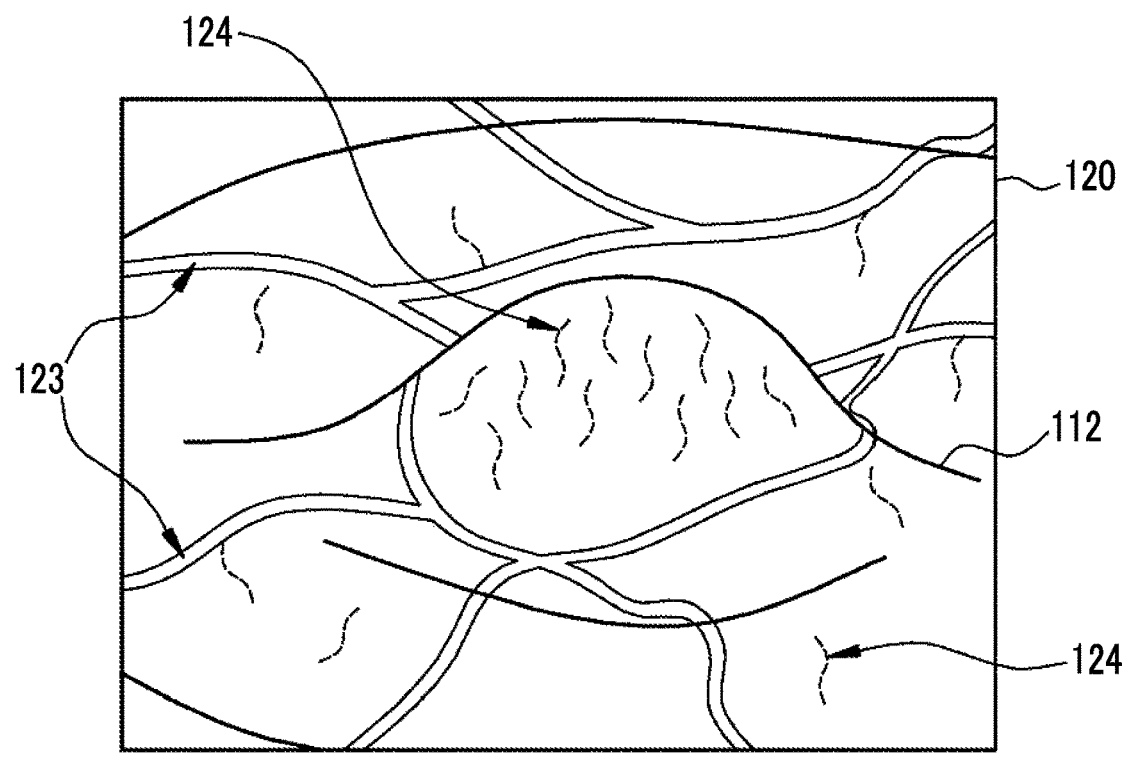
FIG. 13 is a schematic view of a B2 image signal.

Next, in the second light emission mode, the light source 20 generates the blue light B and irradiates the observation object with the generated blue light B (S14), and the imaging sensor 48 images the observation object irradiated with the blue light B (S15). Then, the image signal acquisition unit 53 acquires the B2 image signal corresponding to the blue light B (S16). As illustrated in FIG. 13, since a B2 image signal 120 is an image signal obtained by imaging the observation object with the blue light B, it is possible to observe the surface layer blood vessels 123 at the relatively deep position in addition to the shapes 112 of the observation object. Additionally, the extreme surface layer blood vessels 124 can also be observed with the B2 image signal 120. The B2 image signal at the first timing T1 is transmitted to the image blurring detection unit 70 via various processing units.

In addition, in a case where the B1 image signal 110 is compared with the B2 image signal 120, the contrast of the extreme surface layer blood vessels 124 is higher in the B1 image signal 110, and the contrast of the surface layer blood vessels 123 at the relatively deep position is higher than that of the extreme surface layer blood vessels 124 in the B2 image signal 120.

Next, the image blurring detection unit 70 detects the image blurring amount regarding the B2 image signal at the first timing T1 (S17). The B2 image signal of which the image blurring amount is detected is transmitted to the image selection unit 72. In the image selection unit 72, the B2 image signal with less image blurring to be used for the generation of computed image signal ΔB is selected (S18). In the image selection unit 72, first, it is determined whether or not the image blurring amount of the B2 image signal at the first timing T1 is lower than the threshold value Th1. In a case where the image blurring amount is lower than the threshold value Th1 as a result of the determination, the image selection unit 72 selects the B2 image signal at the first timing T1. The selected B2 image signal at the first timing T1 is transmitted to the alignment processing unit 73. On the other hand, in a case where the image blurring amount exceeds the threshold value Th1, the image selection unit 72 selects the B2 image signal, which is closest to the first timing T1 in time and of which the image blurring amount is lower than the threshold value Th1, from the B2 image signals at the second timing T2 to the N-th timing TN stored in the image signal storage unit 71. The selected B2 image signal is transmitted to the alignment processing unit 73.

Figure 14:
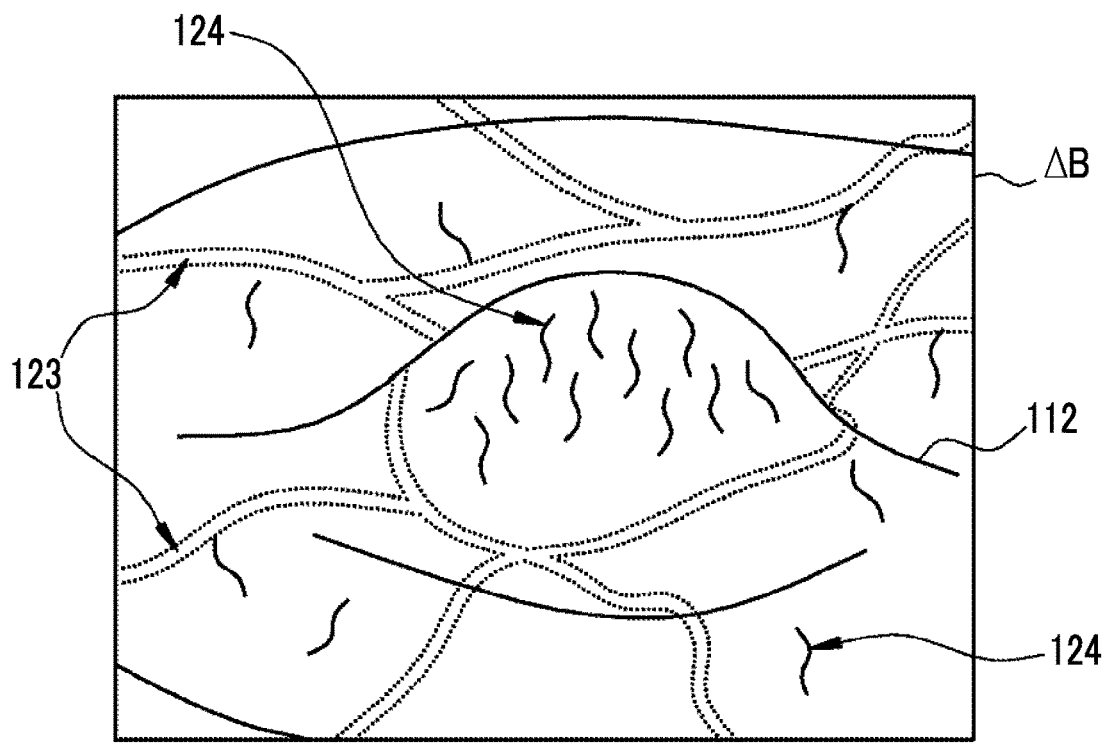
FIG. 14 is a schematic view of a computed image signal.
Figure 15:
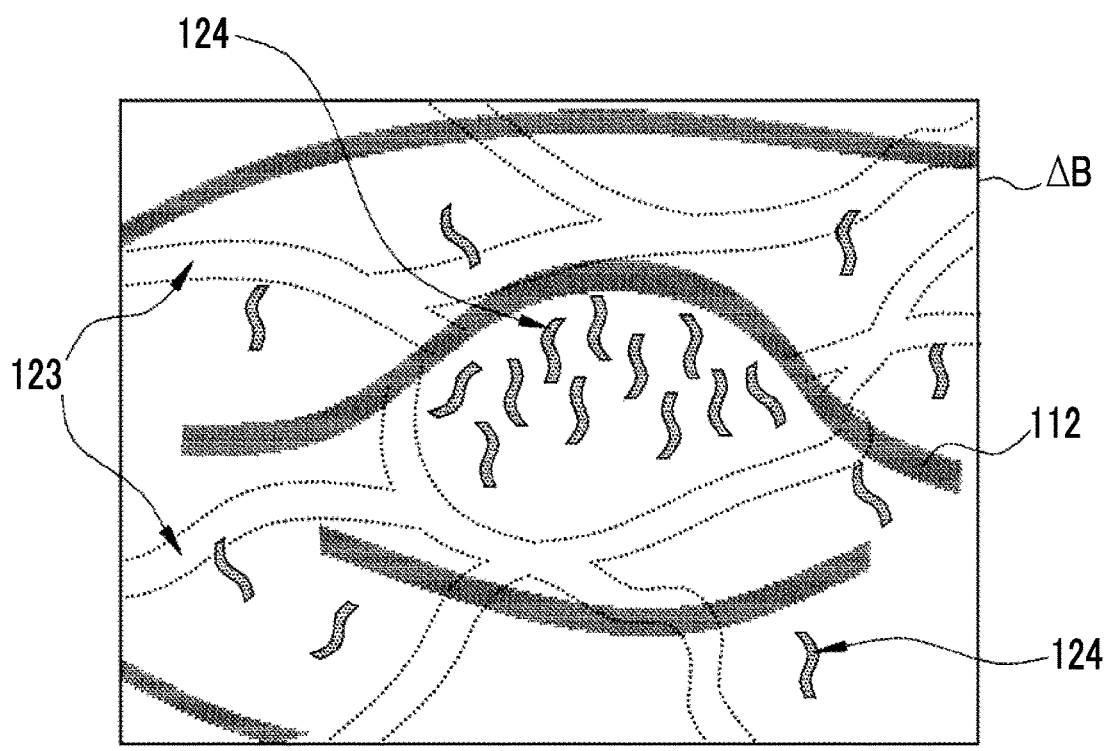
FIG. 15 is a schematic view of the computed image signal after resolution reduction processing.

In the alignment processing unit 73, the alignment between the B1 image signal and the B2 image signal is performed (S19). Then, after brightness correction processing is performed by the brightness correction processing unit 74 (S20), input to the computed image signal generation unit 76 is made. The computed image signal ΔB is generated in the computed image signal generation unit 76 (S21). In the computed image signal ΔB, with respect to an original image signal (for example, the B1 image signal of FIG. 12 or the B2 image signal of FIG. 13), the pixel values of the surface layer blood vessels 123 at the relatively deep position are small, and the pixel values of the extreme surface layer blood vessels 124 are large. For this reason, as illustrated in FIG. 14, in the computed image signal ΔB, the difference between the extreme surface layer blood vessels 124 and the surface layer blood vessels 123 at the relatively deep position becomes more conspicuous than the original image signal. In the computed image signal generation unit 76, in a case where the computed image signal ΔB is generated, the resolution of the computed image signal ΔB is further reduced by the resolution reduction processing unit 77 (S22). As illustrated in FIG. 15, in the computed image signal ΔB that has passed through the resolution reduction processing unit 77, the surface layer blood vessels 123 or the extreme surface layer blood vessels 124 become blurred.

Figure 16:
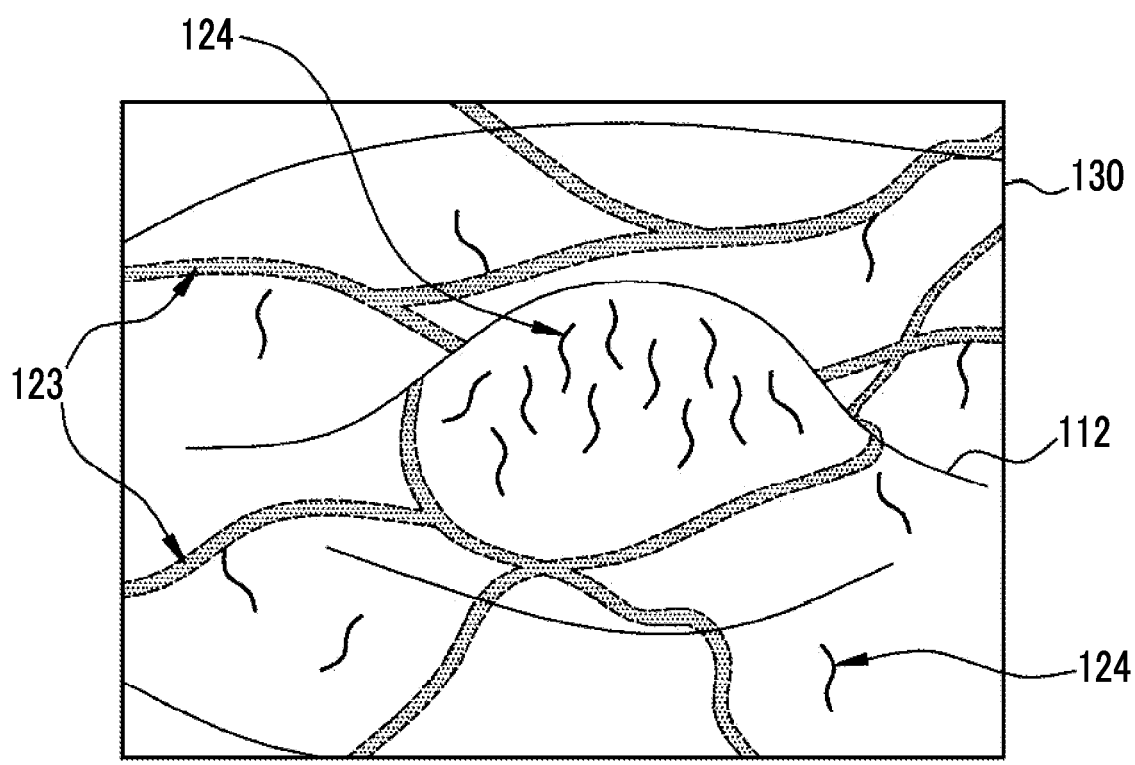
FIG. 16 is a schematic view of the specific depth blood vessel enhanced image.

Thereafter, the special image processing unit 67 allocates the B1 image signal with a high contrast of the extreme surface layer blood vessels 124 to the luminance channel Y and allocates the resolution-reduced computed image signal ΔB to the color difference channels Cr and Cb, thereby generating the specific depth blood vessel enhanced image, using the image generation unit 78 (S23). As illustrated in FIG. 16, in the specific depth blood vessel enhanced image 130, the surface layer blood vessels 123 are colored and displayed in colors of a cyan system, and the extreme surface layer blood vessels 124 are colored and expressed in colors of a magenta system. For this reason, in the specific depth blood vessel enhanced image 130, the extreme surface layer blood vessels 124 and the surface layer blood vessels 123 can be distinguished from each other by colors, and are displayed as an enhanced image that is easy to observe the extreme surface layer blood vessels 124.

As described above, the endoscope system 10 calculates the computed image signal ΔB depending on the difference (or ratio) of the B1 image signal corresponding to the purple light V and the B2 image signal corresponding to the blue light B, allocates an image signal with a high contrast of blood vessels to be enhanced to the luminance channel Y, and allocates the computed image signal ΔB to the color difference channels Cb and Cr. Accordingly, the extreme surface layer blood vessels 124 that are difficult to be distinguished in the related art, and the surface layer blood vessels 123 at the relatively deep position with respect to the extreme surface layer blood vessels 124 can be visualized, enhanced, and displayed with differences in color.

Additionally a difference may occur between the B1 image signal allocated to the luminance channel Y and the computed image signal ΔB due to a difference in the acquisition timing of the B1 image signal and the B2 image signal. As a result, a color deviation may appear in the specific depth blood vessel enhanced image 130. For this reason, in the endoscope system 10, in a case where the computed image signal ΔB is allocated to the color difference channels Cb and Cr, the computed image signal ΔB is allocated to the color difference channels Cb and Cr after the reduction of the resolution by the resolution reduction processing unit 77. Thus, the color deviation is reduced.

Additionally, in a case where the image blurring amount of the B2 image signal becomes excessively large, artifacts may be generated on the specific depth blood vessel enhanced image. For this reason, in the endoscope system 10, the computed image signal ΔB is generated using the B2 image signal with less image blurring selected by the image selection unit 72, and the specific depth blood vessel enhanced image 130 is generated on the basis of the computed image signal ΔB. Accordingly, generation of artifacts is suppressed in the specific depth blood vessel enhanced image 130.

In addition, in the above embodiment, the image generation unit 78 allocates the B1 image signal with a relatively high contrast of the extreme surface layer blood vessels 124 out of the B1 image signal and the B2 image signal to the luminance channel Y, and allocates the computed image signal ΔB to the color difference channels Cb and Cr, thereby generating the specific depth blood vessel enhanced image 130 in which the extreme surface layer blood vessels 124 are selectively enhanced. However, the image generation unit 78 may generate a specific depth blood vessel image in which the surface layer blood vessels 123 at the relatively deep position are enhanced.

In this case, the computed image signal generation unit 76 subtracts the B2 image signal from the B1 image signal after the logarithmic transformation, to generate the computed image signal ΔB, contrary to the above embodiment. Then, the image generation unit 78 allocates the B2 image signal with a high contrast of the surface layer blood vessels 123 at the relatively deep position out of the B1 image signal and the B2 image signal to the luminance channel Y, and allocates the computed image signal ΔB generated by subtracting the B2 image signal from the B1 image signal to the color difference channels Cb and Cr, thereby generating the specific depth blood vessel enhanced image.

The reason why the specific depth blood vessel enhanced image 130 of the above embodiment is capable of enhancing the extreme surface layer blood vessels 124 is because a computed image signal generated by subtracted the B1 image signal from the B2 image signal is used as the computed image signal ΔB. For this reason, in the above embodiment, the image generation unit 78 allocates the B1 image signal with a high contrast of the extreme surface layer blood vessels 124 out of the B1 image signal and the B2 image signal to the luminance channel Y, in a case where the specific depth blood vessel enhanced image 130 in which the extreme surface layer blood vessels 124 are enhanced is generated. However, even in a case where the B2 image signal is allocated to the luminance channel Y, the specific depth blood vessel enhanced image in which the extreme surface layer blood vessels 124 are enhanced can be generated.

In a case where the image generation unit 78 generates the specific depth blood vessel enhanced image, it is preferable to select which of the B1 image signal and the B2 image signal is to be allocated to the luminance channel Y. For example, a first allocation mode where the B1 image signal is allocated to the luminance channel Y, and a second allocation mode where the B2 image signal is allocated to the luminance channel Y is prepared as operation modes of the image generation unit 78, and an image can be generated in a mode selected out of the first allocation mode and the second allocation mode.

Additionally, in a case where it is possible to select an image signal to be allocated to the luminance channel Y, the image generation unit 78 may automatically select the image signal to be allocated to the luminance channel Y. For example, the B1 image signal may be compared with the B2 image signal, and both the image signals or an image signal with less noise within a specified region of interest may be automatically allocated to the luminance channel Y, or both the image signals or an image signal with a higher contrast within the specified region of interest may be automatically allocated to the luminance channel Y.

Figure 17:
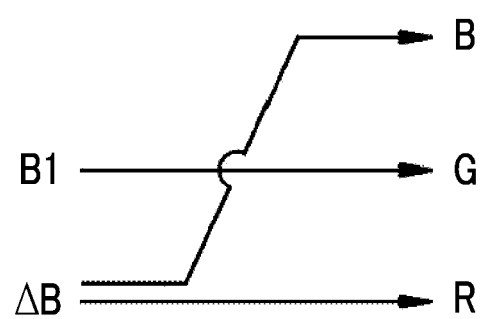
FIG. 17 is an illustrative view illustrating a method of generating a specific depth blood vessel enhanced image of a modification example.

Additionally, in the above embodiment, the image generation unit 78 allocates the B1 image signal to the luminance channel Y, and allocates the computed image signal ΔB to the color difference channels Cb and Cr, thereby generating the specific depth blood vessel enhanced image 130 of YCbCr. However, an image in the RGB format having the R channel, the G channel, and the B channel may be generated. In this case, as illustrated in FIG. 17, the image generation unit 78 allocates the B1 image signal to the G channel that most contributes to brightness, and allocates the computed image signal ΔB to the remaining B channel and R channel.

Figure 18:
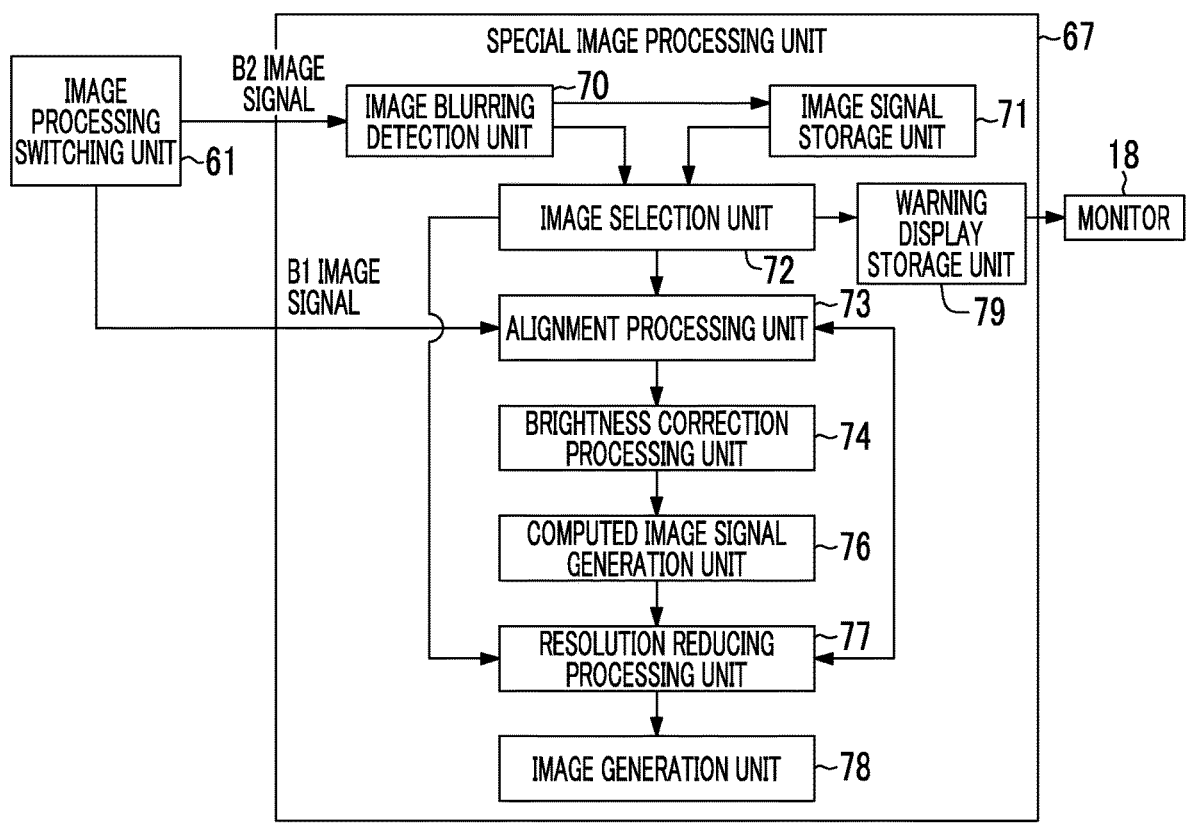
FIG. 18 is a block diagram illustrating a cooperation relationship between an alignment processing unit and a resolution reduction processing unit, and a cooperation relationship between an image selection unit 72 and the resolution reduction processing unit.

In the above embodiment, the cut-off frequency of the LPF to be used in the resolution reduction processing unit 77 is set in advance. However, it is preferable to make the cut-off frequency of the LPF variable and dynamically set the cut-off frequency of the LPF. For example, as illustrated in FIG. 18, the alignment accuracy of the B1 image signal and the B2 image signal is input from the alignment processing unit 73 to the resolution reduction processing unit 77. Then, the resolution reduction processing unit 77 changes the cut-off frequency (the intensity of the resolution reduction processing) of the LPF in accordance with the alignment accuracy of the B1 image signal and the B2 image signal.

Specifically, as the alignment accuracy of the B1 image signal and the B2 image signal is higher, the cut-off frequency of the LPF may be set to a higher frequency to make the intensity of the resolution reduction processing smaller, and as the alignment accuracy of the B1 image signal and the B2 image signal is lower, the cut-off frequency of the LPF may be set to a lower frequency to make the intensity of the resolution reduction processing larger. By doing in this way, the degree of reduction of resolution of the computed image signal ΔB by the resolution reduction processing unit 77 can be optimized, and the blood vessels (for example, the extreme surface layer blood vessels 124) at the specific depth can be appropriately enhanced and displayed.

Additionally, the image blurring amount of the B2 image signal selected the image selection unit 72 among the image blurring amounts detected in the image blurring detection unit 70 may be input to the resolution reduction processing unit 77, and the cut-off frequency (the intensity of the resolution reduction processing) of the LPF may be changed in accordance with to the input image blurring amount. Specifically, as the image blurring amount is smaller, the cut-off frequency of the LPF may be set to a higher frequency to make the intensity of the resolution reduction processing smaller, and as the image blurring amount is larger, the cut-off frequency of the LPF may be set to a lower frequency to make the intensity of the resolution reduction processing larger. Accordingly, since the degree of reduction of resolution of the computed image signal ΔB by the resolution reduction processing unit 77 can be optimized, the specific depth blood vessel enhanced images with less artifacts can be further displayed.

In addition, in a case where the specific depth blood vessel enhanced image is displayed or saved as a still image, it is preferable the cut-off frequency of the LFP is set to be at least within a range where at least a frequency of ⅛ or less of the Nyquist frequency is left, with the resolution of the specific depth blood vessel enhanced image to be generated as a reference.

In the above modification example, the resolution reduction processing unit 77 regulates the intensity of the resolution reduction processing in accordance with the accuracy of alignment processing of the alignment processing unit 73. However, contrary to this, the alignment processing unit 73 may regulate the accuracy of alignment processing in accordance with the intensity of the resolution reduction processing performed by the resolution reduction processing unit 77. In this case, the alignment processing unit 73 set the alignment accuracy of the B1 image signal and the B2 image signal to a higher value as the cut-off frequency of the LPF is set to be larger and the intensity of the resolution reduction processing is set to be smaller.

In a case where the accuracy of alignment processing of the B1 image signal and the B2 image signal performed by the alignment processing unit 73 is made variable and the still image of the specific depth blood vessel enhanced image is displayed or saved, and in a case where a moving image of the specific depth blood vessel enhanced image is displayed, it is preferable to change the accuracy of alignment processing. For example, in a case where the moving image constituted of the specific depth blood vessel image is displayed on the monitor 18, the alignment processing unit 73 aligns the B1 image signal and the B2 image signal with each other with a first accuracy lower than that in a case where the still image of the specific depth blood vessel image is displayed (or saved) on the monitor 18. Contrary to this, in a case where the still image of the specific depth blood vessel image is displayed on the monitor 18, the alignment processing unit 73 aligns the B1 image signal and the B2 image signal with each other with a second accuracy higher than that in a case where the moving image of the specific depth blood vessel image is displayed on the monitor 18. By doing in this way, at the time of the display of the moving image, the specific depth blood vessel enhanced image can be generated at high speed within a range where the color deviation is not conspicuous, and at the time of the acquisition of a still image with a conspicuous color deviation, the specific depth blood vessel enhanced image without a color deviation can be generated.

Additionally, the alignment processing unit 73 may change the alignment accuracy of the B1 image signal and the B2 image signal depending on the size of a specific depth blood vessel image to be generated. For example, in a case where the specific depth blood vessel image to be generated is large, a slight positional deviation is also conspicuous. Thus, the alignment processing unit 73 performs the alignment of the B1 image signal and the B2 image signal with high accuracy. In a case where the specific depth blood vessel image to be generated is small, a slight positional deviation is also conspicuous. Thus, the alignment of the B1 image signal and the B2 image signal is performed with low accuracy. Additionally, contrary to this, the alignment processing unit 73 may perform the alignment of the B1 image signal and the B2 image signal with low accuracy in a case where the specific depth blood vessel image to be generated is large, and may perform the alignment of the B1 image signal and the B2 image signal with high accuracy in a case where the specific depth blood vessel image to be generated is small. By doing in this way, a processing burden on the processor device 16 can be optimized.

As described above, in a case where the alignment processing unit 73 changes the accuracy of alignment processing at the time of the display of the moving image and the acquisition of the still image or in a case where the alignment processing unit 73 changes the alignment accuracy in accordance with to the size of the specific depth blood vessel image, it is preferable that the resolution reduction processing unit 77 changes the cut-off frequency of the LPF depending on the alignment accuracy. For example, at the time of the display of the moving image, the alignment processing unit 73 may lower the alignment accuracy of the B1 image signal and the B2 image signal, and instead this, the cut-off frequency of the LPF may be shifted to a low-frequency side in the resolution reduction processing unit 77. Additionally, at the time of the acquisition of the still image, the alignment processing unit 73 may raise the alignment accuracy of the B1 image signal and the B2 image signal, and instead of this, the cut-off frequency of the LFP signal may be shifted to a high-frequency side in the resolution reduction processing unit 77. That is, at the time of the display of the moving image, a priority may be given to the LPF of the resolution reduction processing unit 77 in which the processing burden on the processor device 16 is small, and at the time of the acquisition of the still image, a priority may be given to the accurate alignment by the alignment processing unit 73.

Additionally, the alignment processing unit 73 may change the alignment accuracy of the B1 image signal and the B2 image signal in accordance with the image blurring amount of the B2 image signal selected in the image selection unit 72. For example, in a case where the image blurring amount is large, it becomes difficult to align the B1 image signal and the B2 image signal with each other. Therefore, it is preferable that the alignment processing unit 73 performs the alignment of the B1 image signal and the B2 image signal with high accuracy. In contrast, in a case where the image blurring amount is small, it is easy to align the B1 image signal and the B2 image signal with each other, the alignment of the B1 image signal and the B2 image signal is performed with low accuracy. The processing burden on the processor device 16 can be optimized by changing the alignment accuracy according to he image blurring amount as mentioned above.

In addition, the alignment processing unit 73 may not perform the alignment of the B1 image signal and the B2 image signal at the time of the display of the moving image, and ay perform the alignment of the B1 image signal and the B2 image signal only at the time of the acquisition of the still image.

In the above embodiment, although the resolution reduction processing unit 77 reduces the resolution of the computed image signal ΔB by the LPF, the resolution can also be reduced by reducing the computed image signal Δ instead of the LPF and then enlarging the computed image signal up to its original size. In this way, in a case where the computed image signal ΔB is reduced and enlarged to reduce the resolution, it is preferable to adopt a reduction method with less aliasing at the time of reduction of the computed image signal ΔB. For example, the computed image signal ΔB can be reduced in resolution after being reduced by the area average method and then enlarged by cubic spline interpolation.

In the above embodiment, although the purple light V is used as the illumination light in the first light emission mode and the blue light B is used as the illumination light in the second light emission mode, two kinds of illumination light having mutually different wavelength ranges to be used in the special observation mode may be light of other wavelength ranges. By changing wavelength ranges, the specific depth blood vessel image in which the depth of the blood vessels to be enhanced is arbitrarily changed can be obtained.

Additionally, the B color filter of the imaging sensor 48 also has sensitivity to the green light G (refer to FIG. 6). Also, light of a wavelength range capable of being received at the B pixel in reflected light or the like of the green light G, and light of a wavelength range capable of being received at the G pixel in the reflected light or the like of the green light G have a difference in the scattering coefficient of the observation object, and have substantially the same light absorption coefficient of hemoglobin. For this reason, for example, only the green light G can be used as the illumination light, and a $B_G$ image signal that is output as the B pixel images the observation object irradiated with the green light G, and a $G_G$ image signal that is output as the G pixel images the observation object irradiated with the green light G can be used instead of the B1 image signal and the B2 image signal embodiment. In this way, in a case where the $B_G$ image signal and the $G_G$ image signal, for example, middle-depth blood vessels at a relatively shallow position among middle-depth blood vessels or middle-depth blood vessels at a relatively deep position among the middle-depth blood vessels can be classified, enhanced, and displayed from the middle-depth blood vessels.

Similarly, the R color filter of the imaging sensor 48 has sensitivity to the green light G (FIG. 6), and light of a wavelength range capable of being received at the G pixel in the reflected light or the like of the green light G, and light of a wavelength range capable of being received at the R pixel in the reflected light or the like of the green light G have a difference in the scattering coefficient of the observation object, and have substantially the same light absorption coefficient of hemoglobin. For this reason, the light source 20 can use broadband green light G including the first illumination light and the second illumination light to be used in the special observation mode as the illumination light, and can use a $G_G$ image signal (first image signal) that is output as the G pixel images the observation object irradiated with the green light G, and a $R_G$ image signal (second image signal) that is output as the R pixel images the observation object irradiated with the green light G instead of the B1 image signal and the B2 image signal embodiment. That is, in a case where the light source 20 generates the broadband illumination light including the first illumination light and the second illumination light like the green light G, the image signal acquisition unit 53 can acquire the first image signal from the B pixel or the G pixel, and can acquire the second image signal from the G pixel or the R pixel.

Additionally, a signal corresponding to the purple light V and the blue light B received by the G color filter of the imaging sensor 48 may be supplemented by utilizing the fact that the imaging sensor 48 may also have sensitivity to the purple light V or the blue light B. For example, in a case where the purple light V is radiated, a signal value corresponding to the purple light V can be increased by adding a signal value obtained from the G pixel to a signal value obtained from the B pixel. Similarly, in a case where the blue light B is radiated, a signal value corresponding to the blue light B can be increased by adding the signal value obtained from G pixel.

As in the above embodiment, it is preferable that, in a case where the extreme surface layer blood vessels 124 are strictly distinguished from the surface layer blood vessels 123 and are enhanced and displayed, it is preferable that both the wavelength ranges of the first illumination light and the second illumination light are within a wavelength range of 500 nm or less. Specifically, as in the above embodiment, it is preferable to use the purple light V having a central wavelength at 405±10 nm and the blue light B having a central wavelength at 460±10 nm as the first illumination light and the second illumination light. It is more preferable to use the purple light V having a central wavelength at 405±10 nm and blue light having a central wavelength at 445±10 nm as the first illumination light and the second illumination light. The blue light having the central wavelength at 445±10 nm can be generated from the above blue light B, for example, by using an optical filter for cutting a long wavelength side of the B-LED 23b in a light path of the B-LED 23b. Additionally, the B-LED 23b may be replaced with another LED that emits the blue light having the central wavelength at 445±10 nm.

In a case where the middle-depth blood vessels are divided into the middle-depth blood vessels at the relatively shallow position and the middle-depth blood vessel at the relatively deep position and enhanced and displayed, it is preferable that both the wavelength ranges of the first illumination light and the second illumination light are 500 nm or more. Specifically, it is preferable to use light having a wavelength of about 500 nm and light having a wavelength of about 600 nm as the first illumination light and the second illumination light.

In addition, in the above embodiment, the computed image signal generation unit 76 generates the computed image signal ΔB representing the traveling pattern of the extreme surface layer blood vessels 124 at the specific depth under the mucous membrane. Instead, however, a computed image signal D showing blood vessel density, or a computed image signal S representing the oxygen saturation (hereinafter referred to as the oxygen saturation of blood vessels) of hemoglobin included in the blood vessels or the like.

The computed image signal D representing the blood vessel density can be calculated using the computed image signal ΔB of the above embodiment. For example, since the computed image signal ΔB of the above embodiment is an image signal from which the extreme surface layer blood vessels 124 are extracted (refer to FIG. 14), the computed image signal D representing the blood vessel density of the extreme surface layer blood vessels 124 can be generated by calculating the ratio of the area of the extreme surface layer blood vessels 124 in a unit area for each pixel using the computed image signal ΔB. In a case where the computed image signal D is generated in this way, the image generation unit 78 allocates the B1 image signal to the luminance channel Y and allocates the computed image signal D to the color difference channels Cb and Cr, thereby generating a blood vessel density image representing the blood vessel density of the extreme surface layer blood vessels 124. The blood vessel density image can give a direct indication to diagnosis, such as stage discrimination of Barrett's adenocarcinoma.

In a case where the computed image signal S representing the oxygen saturation of the blood vessels is generated, for example, the first blue light, the green light G, and the red light R having a central wavelength of 445±10 nm are radiated to image the observation object, and the second blue light, the green light G, and the red light R having a central wavelength of 473±10 nm are irradiated to image the observation object. The first blue light (first illumination light) can be generated from the blue light B by using a first optical filter (for example, an optical filter that cuts a long wavelength side of the blue light B) that limits the wavelength range of the blue light B emitted by the B-LED 23b so as to have the above central wavelength of 445±10 nm. Similarly, the second blue light (second illumination light) can be generated from the blue light B by using a second optical filter (for example, an optical filter that cuts a short wavelength side of the blue light B) that limits the wavelength range of the blue light B emitted by the B-LED 23b so as to have the above central wavelength of 473±10 nm.

The above first blue light has a wavelength range (equal absorption wavelength) that does not almost have a difference in the light absorption coefficients of the oxygenated hemoglobin and the reduced hemoglobin. Meanwhile, the above second blue light has a wavelength range (different absorption wavelength) having a difference in the light absorption coefficients of the oxygenated hemoglobin and the reduced hemoglobin. A ratio or difference between an image signal (first image signal) of an equal absorption wavelength that is obtained as the B pixel images the observation object irradiated with the first blue light, and an image signal (second image signal) of a different absorption wavelength that is obtained as the B pixel images the observation object irradiated with the second blue light has a correlation with oxygen saturation.

Hence, a correlation that associates the ratio or difference between the image signal of equal absorption wavelength and the image signal of different absorption wavelength with the oxygen saturation is calculated in advance by experiments or the like, and the computed image signal generation unit 76 holds this correlation in advance. Then, the computed image signal generation unit 76 calculates the ratio or difference between the image signal of equal absorption wavelength and the image signal of different absorption wavelength to compare the ratio or difference with the above correlation, thereby generating the computed image signal S in which each pixel represents the value of the oxygen saturation of the observation object. Similar to the normal image processing unit 66, the image generation unit 78 radiates the first blue light, the green light G, and the red light R to generate a normal image signals using each image signal obtained by imaging the observation object. Then, an oxygen saturation image representing the oxygen saturation of the observation object is generated by allocating the normal image signal to the luminance channel Y and allocating the computed image signal S representing the oxygen saturation to the color difference channels Cb and Cr. The oxygen saturation image generated in this way can display information useful for diagnosis referred to as the oxygen saturation.

In addition, in a case where the oxygen saturation image is generated using the computed image signal S, it is preferable to detect the image blurring amount of any image signal of the image signal of equal absorption wavelength and the image signal of different absorption wavelength, and select selects the image signal of which the image blurring amount is lower than the threshold value Th1. For example, in a case where the image signal of different absorption wavelength is selected, the image blurring detection unit 70 detects the image blurring amount of the image signal of different absorption wavelength at the first timing. Then, the image selection unit 72 selects the image signal of different absorption wavelength that is lower than the threshold value Th1, from the image signal of different absorption wavelength at the first timing T1, and the image signal of different absorption wavelength at the second timing T2 to the N-th timing TN stored in the image signal storage unit 71.

Then, the computed image signal generation unit 76 generates the computed image signal S on the basis of the image signal of equal absorption wavelength and the selected image signal of different absorption wavelength. Since the computed image signal S is obtained by the computation based on the image signal of different absorption wavelength with less image blurring, the computed image signal S accurately represents the information on the oxygen saturation. Hence, the oxygen saturation image generated on the basis of the above computed image signal S is an image with less artifacts that is accurately colored according to the oxygen saturation.

Figure 19:
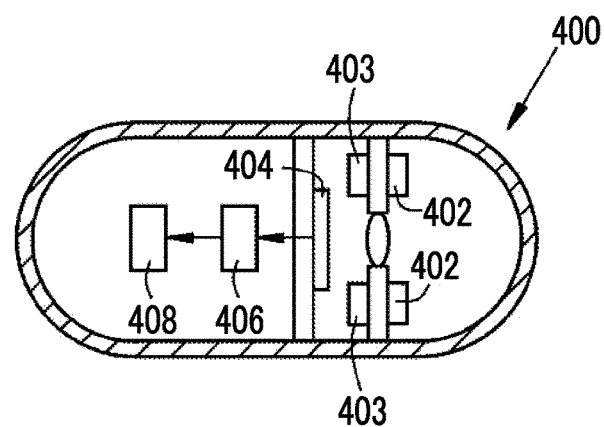
FIG. 19 is a schematic view of a capsule endoscope.

In addition, in the above embodiment, the invention is carried out by the endoscope system 10 that performs observation by inserting the endoscope 12 provided with the imaging sensor 48 into a subject. However, the invention is also suitable for a capsule endoscope system. For example, as illustrated in FIG. 19, the capsule endoscope system has at least a capsule endoscope 400 and a processor device (not illustrated).

The capsule endoscope 400 includes a light source 402, a light source control unit 403, an imaging sensor 404, a signal processing unit 406, and a transmission/reception antenna 408. The light source 402 is configured similarly to the light source 20 of the above embodiment. The light source control unit 403 controls driving of the light source 402, similarly to the light source control unit 22 of the above respective embodiment. Additionally, the light source control unit 403 is capable of wirelessly communicating with a processor device of a capsule endoscope system by the transmission/reception antenna 408. Although the processor device of the capsule endoscope system is substantially the same as the processor device 16 of the above respective embodiment, the signal processing unit 406 has functions of the normal image processing unit 66 and the special image processing unit 67. The blood vessel enhanced image signal or the like generated by the signal processing unit 406 is transmitted to the processor device via the transmission/reception antenna 408. The imaging sensor 404 is configured similarly to the imaging sensor 48 of the above respective embodiment.

Second Embodiment

A second embodiment is different from the first embodiment in an image selection method in the image selection unit 72. The others are substantially the same as those of the first embodiment. In the second embodiment, the image selection unit 72 compares the image blurring amount of the B2 image signal at the first timing T1 with the image blurring amount of the B2 image signal at the second timing T2 stored in the image signal storage unit 71, and selects the B2 image signal with a smaller image blurring amount. Alternatively, the image selection unit 72 selects the B2 image signal with the smallest image blurring amount from the B2 image signal at the first timing T1, the B2 image signal at the second timing T2, . . . , the B2 image signal at the n-th timing, . . . , and the B2 image signal at the N-th timing TN.

In addition, even in the B2 image signal with the smallest image blurring amount among the B2 image signal at the first timing T1 to the B2 image signal at the N-th timing TN, in a case where the image blurring amount of the B2 image signal exceeds a preset threshold value Th2 (may be the same as or different from Th1 of the first embodiment), it is preferable that the image selection unit 72 does not select the B2 image signals at any of the timings. In this case, it is preferable that the computed image signal generation unit 76 generates the computed image signal only on the basis of the B1 image signal, or does not generate the computed image signal. Additionally, the warning display control unit 79 may be made to perform the control of displaying a warning.

Third Embodiment

Figure 20:
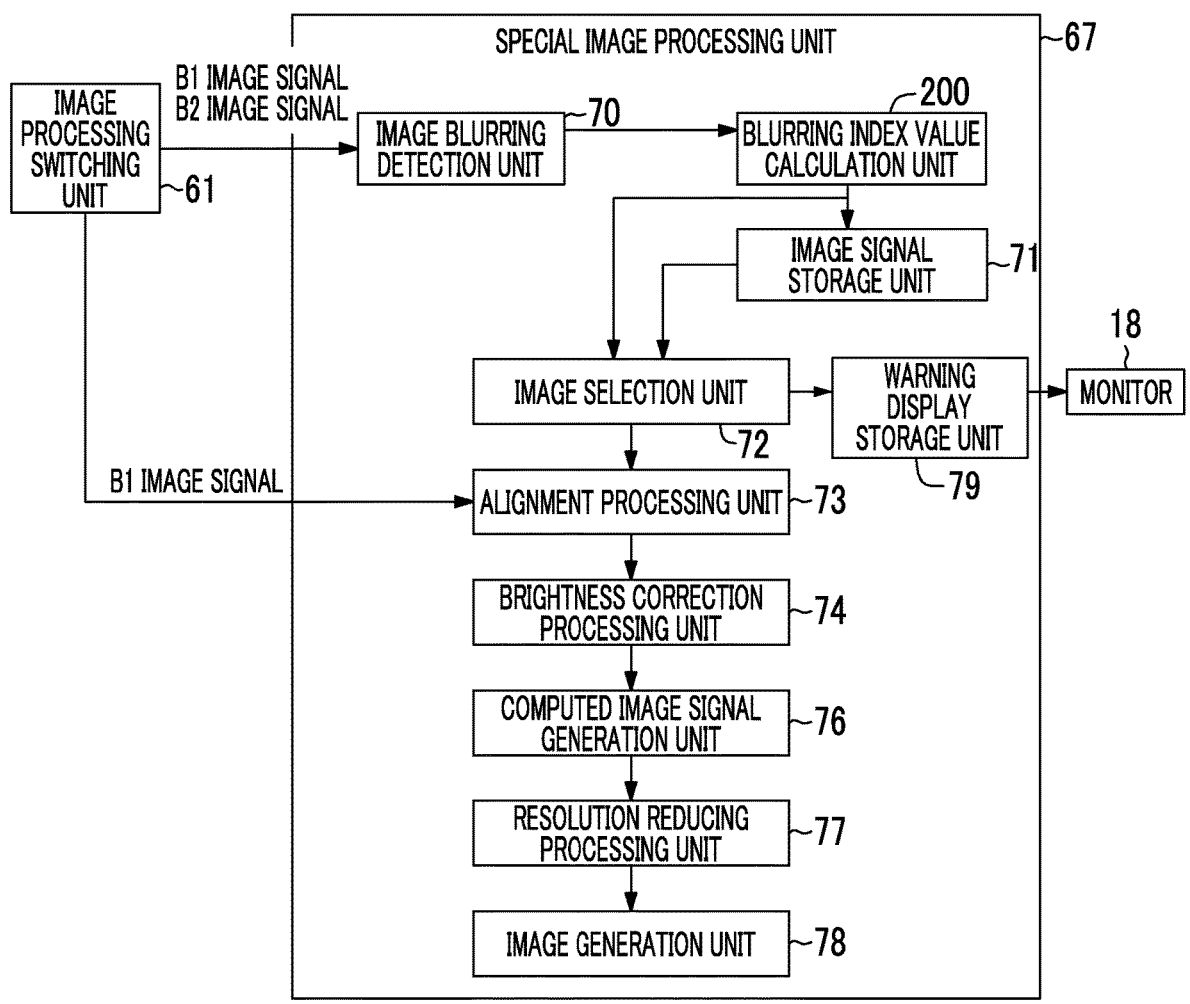
FIG. 20 is a block diagram illustrating the functions of a special image processing unit of a third embodiment.

A third embodiment is different from the first and second embodiments in an image selection method in the image selection unit 72. The others are substantially the same as those of the first embodiment. In a third embodiment, in a case where the special observation mode is set, as illustrated in FIG. 20, the B1 image signal and the B2 image signal among the image signals output from the image processing switching unit 61 are transmitted to the image blurring detection unit 70, and the B1 image signal is transmitted to the alignment processing unit 73.

The image blurring detection unit 70 also detects not only an image blurring amount Blur2 of the B2 image signal but also an image blurring amount Blur1 of the B1 image signal at all the timings of the first timing T1 to the N-th timing TN. Then, a blurring index value calculation unit 200 calculates a difference (|Blur1−Blur2|) (hereinafter referred to as a "blurring difference") or a ratio (Blur1/Blur2) (hereinafter referred to as a "blurring ratio") between the image blurring amount Blur1 of the B1 image signal and the image blurring amount Blur2 of the B2 image signal as a blurring index value at all the timings of the first timing T1 to the N-th timing TN. In addition, in the blurring index value, as the blurring difference is closer to "0", it is shown that both the image blurring amounts Blur1 and Blur2 are closer to each other in time. In addition, as the blurring ratio is closer to "1", it is shown that both the image blurring amounts Blur1 and Blur2 are closer to each other in time.

Here, the B2 image signal at the first timing T1 are associated with a blurring index value at the first timing T1 and is transmitted to the image selection unit 72. Additionally, the B2 image signals at the second timing T2 to the N-th timing TN are associated with blurring index values at the second timing T2 to the N-th timing TN, and are stored in the image signal storage unit 71. Then, the image selection unit 72 determines whether or not the blurring index value at the first timing T1 satisfies a predetermined reference ST. In a case where the reference ST is satisfied as a result of the determination, the B2 image signal at the first timing T1 is selected, and is transmitted to the alignment processing unit 73. In addition, the "second condition" corresponds to "a case where a blurring index value at a certain timing satisfies the reference ST.

Here, for example, in a case where a blurring index value is the blurring difference, it is preferable that the reference ST is "0" or within a range of a value near "0" (corresponding to the "first specific range"), and in a case where a blurring index value is the blurring ratio, it is preferable that the reference ST is "1" or within a range of a value near "1" (corresponds to the "second specific range"). For example, in a case where the image blurring amount of any of the B1 image signal and the B2 image signal is large, artifacts are likely to be generated on the specific depth blood vessel enhanced image. In this case, since the blurring difference deviates from the first specific range and the blurring ratio also deviates from the second specific range, generation of artifacts can be detected from the blurring difference or the blurring ratio. On the other hand, in a case where the image blurring amounts of both the B1 image signal and the B2 image signal are large, artifacts are easily generated on the specific depth blood vessel enhanced image irrespective of occurrence of blurring. In this case, the blurring difference falls within the first specific range and the blurring ratio also falls within the second specific range. For this reason, even in a case where blurring occurs, it is possible to detect the fact that artifacts that greatly influence computation are not generated in the specific depth blood vessel enhanced image, from the blurring difference or the blurring ratio.

In contrast, in a case where the blurring index value at the first timing T1 does not satisfy the reference ST, it is determined whether or not a blurring index value at the second timing T2 satisfies the reference ST. As a result of the determination, in a case where the reference ST is satisfied, the B2 image signal at the second timing T2 is transmitted to the alignment processing unit 73, and in a case where the reference ST is not satisfied, determination based on the same blurring index value is performed for the B2 image signal at the third timing T3, and it is determined whether the image blurring amount should be transmitted to the alignment processing unit 73. The image selection unit 72 performs the same determination as above until the B2 image signal of which the blurring index value satisfies the reference is detected.

In addition, in the image selection unit 72, a positional deviation from the B1 image signal frequently becomes large regarding the B2 image signals at timings excessively separated from the first timing T1 in time. Thus, it is preferable to select the B2 image signal of which the blurring index value satisfies the reference ST and which is closest to the first timing T1 in time. Additionally, in a case where blurring index values of all the B2 image signals at the second timing T2 to the N-th timing TN do not the reference ST, it is preferable that the image selection unit 72 does not select the B2 image signals at any of the timings.

In this way, in a case where the blurring index values of all the B2 image signals at the second timing T2 to the N-th timing TN do not satisfy the reference ST, it is preferable that the computed image signal generation unit 76 generates the computed image signal ΔB only on the basis of the B1 image signals or does not generate the computed image signal ΔB. Additionally, in a case where blurring index values of all the B2 image signals at the second timing T2 to the N-th timing TN do not the reference ST, the control of displaying a warning may be performed by the warning display control unit 79.

In addition, in the third embodiment, the resolution reduction processing unit 77 may change the cut-off frequency of the LPF in accordance with a blurring index value associated with the B2 image signal selected in the image selection unit 72. For example, in a case where a blurring index value is the blurring difference, as the cut-off frequency of the LPF is closer to "0", the cut-off frequency of the LPF may be set to a higher frequency to make the intensity of the resolution reduction processing smaller, and as the cut-off frequency of the LPF is separated from "0", the cut-off frequency of the LPF may be set to a lower frequency to make the intensity of the resolution reduction processing larger.

Additionally, the alignment processing unit 73 may change the alignment accuracy of the B1 image signal and the B2 image signal in accordance with the blurring index value associated with the B2 image signal selected in the image selection unit 72. For example, in a case where a blurring index value is the blurring difference and the blurring difference is separated from "0", it is preferable that the alignment processing unit 73 performs the alignment of the B1 image signal and the B2 image signal with high accuracy. In contrast, in a case where the blurring difference is close to "0", it is preferable to perform the alignment of the B1 image signal and the B2 image signal with low accuracy.

Fourth Embodiment

A fourth embodiment is different from the first to third embodiments in an image selection method in the image selection unit 72. The others are substantially the same as those of the third embodiment. In the third embodiment, the image selection unit 72 compares a blurring index value associated with the B2 image signal at the first timing T1 with a blurring index value associated with the B2 image signal at the second timing T2 stored in the image signal storage unit 71, and selected the B2 image signal with a smaller blurring index value. Alternatively, the image selection unit 72 selects the B2 image signal with the smallest blurring index value from the B2 image signal at the first timing T1, the B2 image signal at the second timing T2, . . . , the B2 image signal at the n-th timing, . . . , and the B2 image signal at the N-th timing TN.

In addition, even in the B2 image signal with the smallest blurring index value among the B2 image signal at the first timing T1 to the B2 image signal at the N-th timing TN, in a case where the blurring index value of the B2 image signal does not satisfy the preset reference ST (may be the same as or different from ST of the third embodiment), it is preferable that the image selection unit 72 does not select the B2 image signals at any of the timings. In this case, it is preferable that the computed image signal generation unit 76 generates the computed image signal only on the basis of the B1 image signal, or does not generate the computed image signal. Additionally, the warning display control unit 79 may be made to perform the control of displaying a warning.

Fifth Embodiment

In a fifth embodiment, the image selection unit 72 has a manual selection mode where the B2 image signal is manually selected while a user views images based on the B2 image signals at the first timing T1 to the N-th timing TN displayed on the monitor 18 and image blurring amounts thereof, in addition to an auto-selection mode where the B2 image signal is automatically selected on the basis of the image blurring amount, and selects the B2 image signal in any set selection mode. Here, an image selection method by the auto-selection mode is the same as the image selection method shown in the first and second embodiments.

Figure 21:
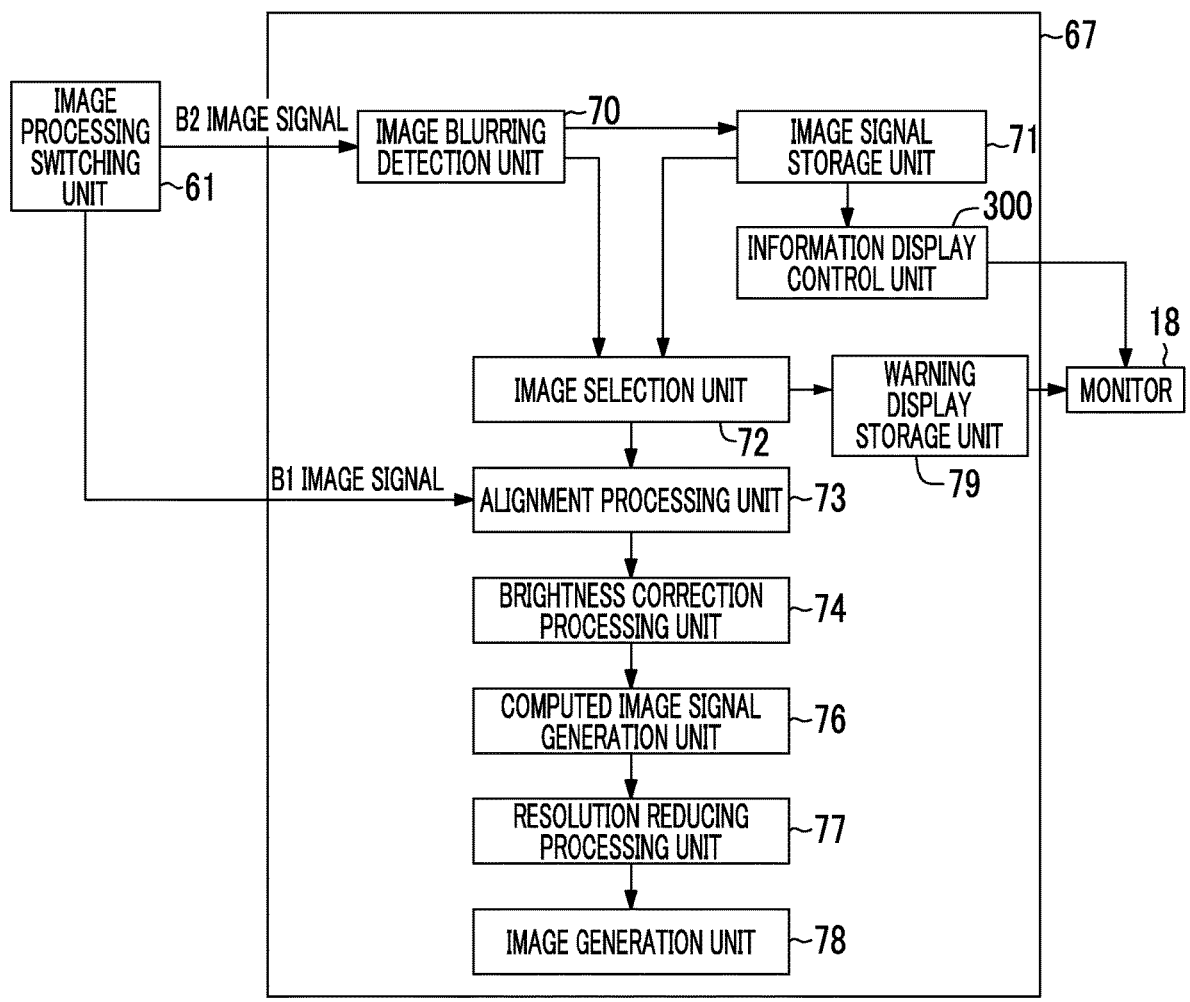
FIG. 21 is a block diagram illustrating the functions of a special image processing unit of a fifth embodiment including a list display control function of image blurring amounts.

Meanwhile, in the fifth embodiment, as illustrated in FIG. 21, an information display control unit 300, which performs the control of displaying information on the image blurring amount, is provided within the special image processing unit 67 shown in the first and second embodiments. In a case where the manual selection mode is set, the information display control unit 300 perform the control of displaying a list of an image (in FIG. 2, displayed as the "B2 image") based on the B2 image signal at each timing and an image blurring amount at the timing together, on the monitor 18, on the basis of the B2 image signals at the first timing T1 to the Nth timing input to the image signal storage unit 71 and the image blurring amounts of the B2 image signals at the first timing T1 to the Nth timing associated with these.

Figure 22:
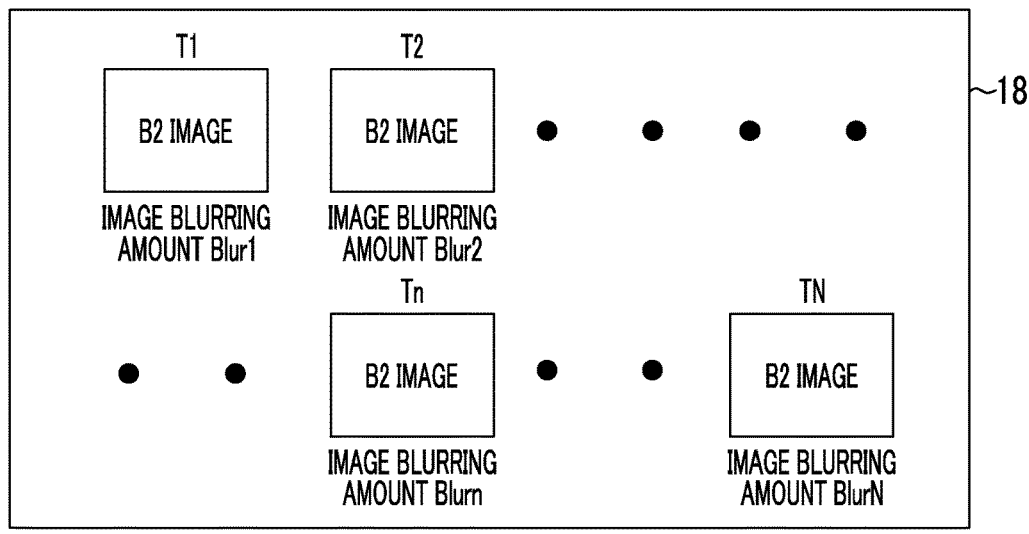
FIG. 22 is an image view of a monitor that display a list of images based on B2 image signals at respective timings and image blurring amounts at respective timings.

As illustrated in FIG. 22, the user while viewing the image and an image blurring amount based on the B2 image signal at each timing displayed on the monitor 18, and selects an optimal B2 image signal suitable for generating the specific depth blood vessel enhanced image. It is preferable that the selection is performed by the console 19. The selected B2 image signal is transmitted to the alignment processing unit 73, similarly to the first and second embodiments. Regarding the image selection by the user as described above, in a case where the user performs the image selection based on the image blurring amount, the selection is performed in the same way as the concept of the image selection by the image selection unit 72 shown in the first embodiment and the second embodiment. On the other hand, in a case where the image selection is performed on the basis of the image based on the basis of the B2 image signal, subjective image selection based on the user's experience rule becomes possible.

Figure 23:
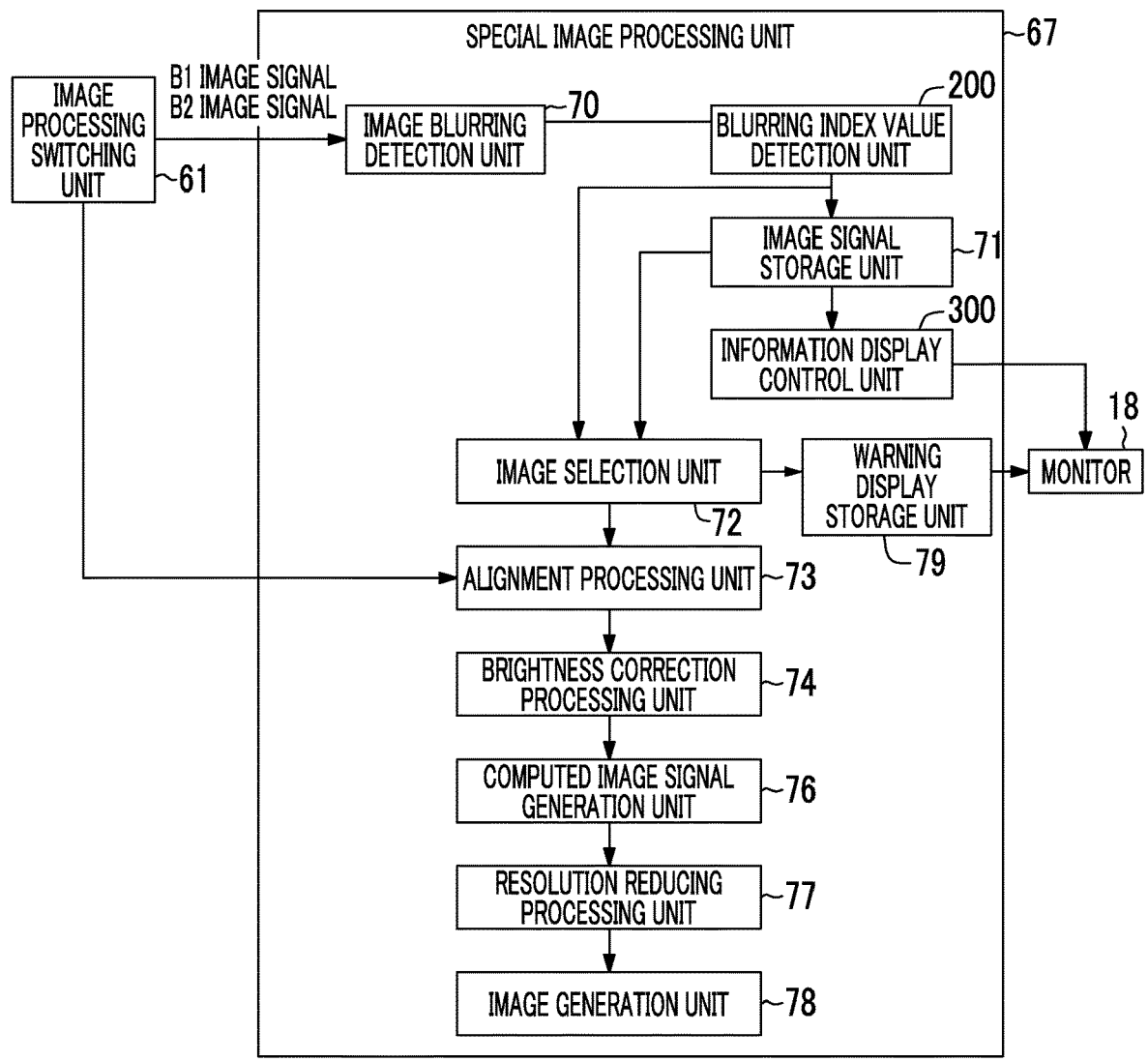
FIG. 23 is a block diagram illustrating the functions of a special image processing unit of a fifth embodiment including a list display control function of blurring index values.

In addition, in the manual selection mode set in the image selection unit 72, as the information to be displayed the monitor 18, the blurring index value may be displayed instead of the image blurring amount. In this case, as illustrated in FIG. 23, the information display control unit 300, which performs the control of displaying the blurring index value, is provided within the special image processing unit 67 shown in the third and fourth embodiments.

Then, in a case where the manual selection mode is set, the information display control unit 300 perform the control of displaying a list of an image based on the B2 image signal at each timing and a blurring index value at the timing together, on the monitor 18, on the basis of the B2 image signals at the first timing T1 to the Nth timing input to the image signal storage unit 71 and the blurring index values at the first timing T1 to the Nth timing associated with these. In addition, the list display including the blurring index value is performed similarly to as the list display (refer to FIG. 22) of displaying the image blurring amount. Additionally, the image selection method by the user is performed similarly to the image selection method based on the image blurring amount.

In addition, in the above first to fifth embodiments, the purple light V and the blue light B having mutually different wavelength ranges are sequentially radiated, respectively. However, the first illumination light and the second illumination light having the same wavelength range may be sequentially radiated, respectively. In this case, by performing computation in which averaging processing of the second image signal selected in the image selection unit 72 out of the first image signal obtained in a case where the first illumination light is radiated and the second image signal obtained in a case where the second illumination light is radiated is performed in the computed image signal generation unit 76, it is possible to reduce the noise of an image after the averaging processing. In addition, in a case where the averaging processing is performed, it is preferable that the image blurring amounts of the first image signal and the second image signal are small, respectively.

EXPLANATION OF REFERENCES

10: endoscope system
12: endoscope
12a: insertion part
12b: operating part
12c: bending part
12d: distal end part
12e: angle knob
13a: mode changeover switch
13b: zooming operating part
14: light source device
16: processor device
18: monitor
19: console
20: light source
22: light source control unit
23a: V-LED
23b: B-LED
23c: G-LED
23d: R-LED
30a: illumination optical system
30b: imaging optical system
41: light guide
45: illumination lens
46: objective lens
47: zoom lens
48: imaging sensor
51: CDS/AGS circuit
52: A/D converter
53: image signal acquisition unit
56: DSP
58: noise removal unit 61: image processing switching unit
66: normal image processing unit
67: special image processing unit
68: video signal generation unit
70: image blurring detection unit
71: image signal storage unit
72: image selection unit
73: alignment processing unit
74: brightness correction processing unit
76: computed image signal generation unit
77: resolution reduction processing unit
78: image generation unit
79: warning display control unit
110: image signal
200: blurring index value calculation unit
300: information display control unit
400: capsule endoscope
402: light source
403: light source control unit
404: imaging sensor
406: signal processing unit
408: transmission/reception antenna

What is claimed is:

1. An endoscope system comprising:
a light source that sequentially generates first illumination light and second illumination light;
an imaging sensor that sequentially images an observation object illuminated sequentially with the first illumination light and the second illumination light at a first timing T1, thereby outputting multi-frame image signals at the first timing T1 and sequentially images the observation object illuminated sequentially with the first illumination light and the second illumination light at a specific timing before the first timing T1, thereby outputting multi-frame image signals at the specific timing;
a processor, configured to:
select a second image signal of which an image blurring amount satisfies a first condition from second image signals obtained in a case where the second illumination light is radiated among the multi-frame image signals at the first timing T1 and the specific timing; and
perform computation based on a first image signal obtained in a case where the first illumination light is radiated among the multi-frame image signals at the first timing T1 and the second image signal, thereby generating a computed image signal.

2. The endoscope system according to claim 1, wherein the processor selects a second image signal, of which the image blurring amount is less than a predetermined threshold value and which is imaged at a timing closest to the first timing T1, as the second image signal that satisfies the first condition.

3. The endoscope system according to claim 1, wherein the processor selects a second image signal with the smallest image blurring amount, as the second image signal that satisfies the first condition.

4. The endoscope system according to claim 1, wherein the processor does not select the second image signal in a case where the second image signal of which the image blurring amount satisfies the first condition is not included in the multi-frame image signals at the first timing T1 and the specific timing, and wherein the processor generates the computed image signal only on the basis of the first image signal.

5. The endoscope system according to claim 1, wherein the processor does not select the second image signal in a case where the second image signal of which the image blurring amount satisfies the first condition is not included in the multi-frame image signals at the first timing T1 and the specific timing, and wherein the processor does not generate the computed image signal.

6. The endoscope system according to claim 1, wherein the processor is further configured to:
perform a control of displaying a warning in a case where the second image signal of which the image blurring amount satisfies the first condition is not included in the multi-frame image signals at the first timing T1 and the specific timing.

7. The endoscope system according to claim 1, wherein the processor is further configured to:
perform a control of displaying an image based on the second image signals included in the multi-frame image signals at the first timing T1 and the specific timing, and image blurring amounts of the second image signals at the first timing T1 and the specific timing on a display,
wherein the processor has an auto-selection mode where the second image signal that satisfies the first condition is automatically selected, and a manual selection mode where a second image signal selected and indicated by a user is selected among the second image signals displayed on the display, and performs image selection in either the auto-selection mode or the manual selection mode.

8. An endoscope system comprising:
a light source that sequentially generates first illumination light and second illumination light;
an imaging sensor that sequentially images an observation object illuminated sequentially with the first illumination light and the second illumination light at a first timing T1, thereby outputting multi-frame image signals at the first timing T1 and sequentially images the observation object illuminated sequentially with the first illumination light and the second illumination light at a specific timing before the first timing T1, thereby outputting multi-frame image signals at the specific timing;
a blurring index value calculation unit that calculates blurring index values at the first timing T1 and the specific timing on the basis of an image blurring amount of a first image signal obtained in a case where the first illumination light is radiated and an image blurring amount of a second image signal obtained in a case where the second illumination light is radiated, among the multi-frame image signals at the first timing T1 and the specific timing;
an image selection unit that selects a second image signal at a timing at which the blurring index values satisfy a second condition among the second image signals included in the multi-frame image signals at the first timing T1 and the specific timing; and
a computed image signal generation unit that performs computation based on a first image signal included in the multi-frame image signals at the first timing T1 and a second image signal selected in the image selection unit, thereby generating a computed image signal.

9. The endoscope system according to claim 8, wherein in a case where the blurring index values are a blurring difference showing a difference between an image blurring amount of the first image signal and an image blurring amount of the second image signal, the image selection unit selects a second image signal at a timing at which the blurring difference is within a first specific range as the second image signal at the timing at which the second condition is satisfied, and wherein in a case where the blurring index values are a blurring ratio showing a ratio of the image blurring amount of the first image signal and the image blurring amount of the second image signal, the image selection unit selects a second image signal at a timing at which the blurring ratio is within a second specific range as the second image signal at the timing at which the second condition is satisfied.

10. The endoscope system according to claim 8,
wherein the processor does not select the second image signal in a case where the blurring index values at any of the timings do not satisfy the second condition, and
wherein the processor generates the computed image signal only on the basis of the first image signal.

11. The endoscope system according to claim 8,
wherein the processor does not select the second image signal in a case where the blurring index values at any of the timings do not satisfy the second condition, and
wherein the processor does not generate the computed image signal.

12. The endoscope system according to claim 8, wherein the processor is further configured to:
perform a control of displaying a warning in a case where the blurring index values at any of the timings do not satisfy the second condition.

13. The endoscope system according to claim 8, wherein the processor is further configured to:
perform a control of displaying an image based on the second image signals included in the multi-frame image signals at the first timing T1 and the specific timing, and the blurring index values at the first timing T1 and the specific timing on a display,
wherein the processor has an auto-selection mode where the multi-frame image signals that satisfy the second condition is automatically selected, and a manual selection mode where a second image signal selected and indicated by a user is selected among the second image signals displayed on the display, and performs image selection in either the auto-selection mode or the manual selection mode.

14. The endoscope system according to claim 1,
wherein the image blurring amount is calculated on the basis of a blood vessel structure or a mucous membrane structure within the first image signal or the second image signal.

15. The endoscope system according to claim 1,
wherein the image blurring amount is calculated on the basis of a central region within the first image signal or the second image signal.

16. The endoscope system according to claim 1,
wherein a plurality of timings of a second timing T2 to an N-th timing TN are included in the specific timing, and wherein N represents an integer of 3 or more.

17. The endoscope system according to claim 1,
wherein the first illumination light and the second illumination light have different wavelength ranges, respectively.

18. A method of operating an endoscope system, the method comprising:
sequentially generating first illumination light and second illumination light by a light source;
sequentially imaging an observation object illuminated sequentially with the first illumination light and the second illumination light at a first timing T1, thereby outputting multi-frame image signals at the first timing T1 and sequentially images the observation object illuminated sequentially with the first illumination light and the second illumination light at a specific timing before the first timing T1, thereby outputting multi-frame image signals at the specific timing, by an imaging sensor;
selecting a second image signal of which an image blurring amount satisfies a first condition from second image signals included in the multi-frame image signals at the first timing T1 and the specific timing, by a processor; and
performing computation based on a first image signal including in the multi-frame image signals at the first timing T1 and the second image signal, thereby generating a computed image signal, by the processor.

19. A method of operating an endoscope system, the method comprising:
sequentially generating first illumination light and second illumination light by a light source;
sequentially imaging an observation object illuminated sequentially with the first illumination light and the second illumination light at a first timing T1, thereby outputting multi-frame image signals at the first timing T1 and sequentially images the observation object illuminated sequentially with the first illumination light and the second illumination light at a specific timing before the first timing T1, thereby outputting multi-frame image signals at the specific timing, by an imaging sensor;
calculating blurring index values at the first timing T1 and the specific timing on the basis of an image blurring amount of a first image signal and an image blurring amount of a second image signal in the multi-frame image signals at the first timing T1 and the specific timing, by a processor;
selecting a second image signal at a timing at which the blurring index values satisfy a second condition among the second image signals included in the multi-frame image signals at the first timing T1 and the specific timing, by the processor; and
performing computation based on a first image signal included in the multi-frame image signals at the first timing T1 and a second image signal included in the multi-frame image signals, thereby generating a computed image signal, by the processor.

20. The method of operating an endoscope system according to claim 18,
wherein the first illumination light and the second illumination light have different wavelength ranges, respectively.

* * * * *